(12) United States Patent
Schuck et al.

(10) Patent No.: US 11,484,502 B2
(45) Date of Patent: Nov. 1, 2022

(54) PHARMACEUTICAL COMPOSITION COMPRISING PDE9 INHIBITOR

(71) Applicant: Eisai R&D Management Co., Ltd., Tokyo (JP)

(72) Inventors: Edgar Schuck, Parsippany, NJ (US); Robert Lai, Hatfield (GB); Ishani Savant Landry, Bernardsville, NJ (US); Bhaskar Rege, Woodcliff Lake, NJ (US); Mai Miyamoto, Tsukuba (JP); Sadaharu Kotani, Tokyo (JP); Kanta Horie, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/609,514

(22) PCT Filed: May 30, 2018

(86) PCT No.: PCT/JP2018/020643
§ 371 (c)(1),
(2) Date: Oct. 30, 2019

(87) PCT Pub. No.: WO2018/221546
PCT Pub. Date: Dec. 6, 2018

(65) Prior Publication Data
US 2020/0078306 A1   Mar. 12, 2020

Related U.S. Application Data

(60) Provisional application No. 62/513,690, filed on Jun. 1, 2017.

(51) Int. Cl.
| | | |
|---|---|---|
| *A61K 9/20* | (2006.01) | |
| *A61P 25/28* | (2006.01) | |
| *A61K 9/16* | (2006.01) | |
| *A61K 9/48* | (2006.01) | |
| *A61K 31/437* | (2006.01) | |

(52) U.S. Cl.
CPC ......... *A61K 9/20* (2013.01); *A61K 9/16* (2013.01); *A61K 9/4808* (2013.01); *A61K 31/437* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 8,563,565 B2 | 10/2013 | Norimine et al. | |
| 2006/0035920 A1 | 2/2006 | Boyle et al. | |
| 2006/0100222 A1 | 5/2006 | Boss et al. | |
| 2009/0131467 A1 | 5/2009 | Kanazawa et al. | |
| 2010/0048556 A1 | 2/2010 | Okada et al. | |
| 2010/0210839 A1 | 8/2010 | Böss et al. | |
| 2011/0082137 A1 | 4/2011 | Giovannini et al. | |
| 2011/0131467 A1 | 6/2011 | Weathers | |
| 2011/0184000 A1 | 7/2011 | Giovannini et al. | |
| 2011/0319385 A1 | 12/2011 | Kaizawa et al. | |
| 2013/0085134 A1 | 4/2013 | Kaizawa et al. | |
| 2013/0143907 A1 | 6/2013 | Norimine et al. | |
| 2013/0225553 A1 | 8/2013 | Kaizawa et al. | |
| 2013/0225572 A1 | 8/2013 | Okada et al. | |
| 2013/0296352 A1 | 11/2013 | Norimine et al. | |
| 2016/0046623 A1* | 2/2016 | Ozaki ............... | A61P 25/28 546/82 |
| 2016/0324852 A1 | 11/2016 | Friedhoff et al. | |
| 2020/0129488 A1 | 4/2020 | Miyamoto et al. | |
| 2020/0129501 A1 | 4/2020 | Miyamoto et al. | |
| 2020/0155541 A1 | 5/2020 | Miyamoto et al. | |

FOREIGN PATENT DOCUMENTS

| | | |
|---|---|---|
| AU | 2008249750 | 11/2008 |
| CA | 2754457 | 9/2010 |
| CN | 101553491 | 10/2009 |
| CN | 101983199 | 3/2011 |
| CN | 102365285 | 8/2014 |
| CN | 105121440 | 12/2015 |
| EA | 200500322 | 8/2005 |
| EP | 0934273 | 8/1999 |
| EP | 1925617 | 5/2008 |
| EP | 2027111 | 2/2009 |
| EP | 2103613 | 9/2009 |
| EP | 2152712 | 2/2010 |
| EP | 2769980 | 8/2014 |
| EP | 2982675 | 2/2016 |
| JP | H5-132484 | 5/1993 |
| JP | H9-506634 | 6/1997 |
| JP | 2006-045118 | 2/2006 |
| JP | 2011-516454 | 5/2011 |
| JP | 2012-515761 | 7/2012 |
| JP | 2013-067595 | 4/2013 |
| JP | 5546693 | 5/2014 |

(Continued)

OTHER PUBLICATIONS

Doose etal (J Clin Pharmacol 36:884-891, 1996) (Year: 1996).*
Office Action in Israeli Patent Application No. 270318, dated Aug. 23, 2020, 5 pages (with English Translation).
Office Action in Israeli Patent Application No. 270357, dated Aug. 23, 2020, 5 pages (with English Translation).
Office Action in Israeli Patent Application No. 270394, dated Aug. 23, 2020, 5 pages (with English Translation).
Office Action in Israeli Patent Application No. 270395, dated Aug. 23, 2020, 5 pages (with English Translation).

(Continued)

*Primary Examiner* — Craig D Ricci
(74) *Attorney, Agent, or Firm* — Fish & Richardson P.C.

(57) ABSTRACT

The present invention provides a pharmaceutical composition comprising a PDE9 inhibitor. Specifically, the PDE9 inhibitor is (S)-7-(2-methoxy-3,5-dimethylpyridin-4-yl)-1-(tetrahydrofuran-3-yl)-1H-pyrazolo[4,3-c]quinolin-4(5H)-one or pharmaceutically acceptable salts thereof.

6 Claims, No Drawings

(56) References Cited

FOREIGN PATENT DOCUMENTS

| MX | 2014/003800 | 7/2014 |
|----|----|----|
| RU | 2383546 | 8/2006 |
| RU | 2426734 | 8/2011 |
| TW | 201321379 | 6/2013 |
| WO | WO 95/32205 | 11/1995 |
| WO | WO 1998/016512 | 4/1998 |
| WO | WO 2003/037899 | 5/2003 |
| WO | WO 2007/032466 | 3/2007 |
| WO | WO 2007/146073 | 12/2007 |
| WO | WO 2007/146115 | 12/2007 |
| WO | WO 2008/072778 | 6/2008 |
| WO | WO 2008/072779 | 6/2008 |
| WO | WO 2008/139293 | 11/2008 |
| WO | WO 2009/121919 | 10/2009 |
| WO | WO 2010/026214 | 3/2010 |
| WO | WO 2010/084438 | 7/2010 |
| WO | WO 2010/101230 | 9/2010 |
| WO | WO 2010/120695 | 10/2010 |
| WO | WO 2012/020022 | 2/2012 |
| WO | WO 2012/033144 | 3/2012 |
| WO | WO 2012/110440 | 8/2012 |
| WO | WO 2013/045400 | 4/2013 |
| WO | WO 2013/051639 | 4/2013 |
| WO | WO 2014/163147 | 10/2014 |

OTHER PUBLICATIONS

Bonkale et al., "Reduced nitric oxide responsive soluble guanylyl cyclase activity in the superior temporal cortex of patients with Alzheimer's disease," Neuroscience Letters, 1995, 187:5-8.
Domek-Łopacińska et al., "Cyclic GMP Metabolism and its role in brain physiology," Journal of Physiology and Pharmacology, 2005, 56:15-34.
Fisher et al., "Isolation and Characterization of PDE9A, a Novel Human cGMP-specific Phosphodiesterase," The Journal of Biological Chemistiy, 1998, 273(25):15559-15564.
International Search Report and Written Opinion in International Application No. PCT/JP2018/020643, dated Aug. 21, 2018, 4 pages.
Van der Staay et al., "The novel selective PDE9 inhibitor BAY 73-6691 improves learning and memory in rodents," Neuropharmacology, 2008, 55:908-918.
Wang et al., "Cyclic GMP-Dependent Protein Kinase and Cellular Signaling in the Nervous System," Journal of Neurochemistiy, 1997, 68:443-456.
International Preliminary Report on Patentability in International Application No. PCT/JP2018/02063 8, dated Dec. 12, 2019, 7 pages.
International Preliminary Report on Patentability in International Application No. PCT/JP2018/020649, dated Dec. 12, 2019, 6 pages.
International Preliminary Report on Patentability in International Application No. PCT/JP2018/020650, dated Dec. 12, 2019, 8 pages.
Bergman et al., "Successful Use of Donepezil for the Treatment of Psychotic Symptoms in Patients With Parkinson's Disease," Clinical Neuropharmacology, Mar.-Apr. 2002, 25(2):107-110.
Bourke et al., "Possible association between donepezil and worsening Parkinson's disease," The Annals of Pharmacotherapy, 1998, 32:610-611.
Brandon and Rotella, "Potential CNS—14 Applications for Phosphodiesterase Enzyme Inhibitors," Annual Reports in Medicinal Chemistiy, 2007, 42:3-12.
Chinese Observations in Application No. 201480016592.4, dated Nov. 4, 2015, 2 pages, (with English Translation).
Cummings et al., "Pimavanserin for patients with Parkinson's disease psychosis: a randomised, placebo-controlled phase 3 trial," The Lancet, Feb. 2014, 383(9916):533-540.
Dubois et al., "Donepezil in Parkinson's Disease Dementia: A Randomized Double-Blind Efficacy and Safety Study," Movement Disorders, Sep. 2012, 27(10):1230-1238.
Eisai Co. Ltd. [Online], "Press Conference; Materials in reporter meeting," Mar. 2017, [Retrieved on Jul. 3, 2018], Retrieved from: URL<https://www.eisai.co.jp/ir/library/presentations/pdf/4523_170309>, 96 pages (with English Translation).
European Response to Office Action in Application No. 14780073. 4, dated May 11, 2016, 5 pages.
European Response to Office Action in Application No. 14780139. 3, dated May 10, 2016, 4 pages.
European Search Report in Application No. 14780073.4, dated Jul. 28, 2016, 4 pages.
European Search Report in Application No. 14780139.3, dated Jul. 13, 2016, 5 pages.
Extended European Search Report in European Application No. 12837953.4, dated Jan. 27, 2015, 10 pages.
Gauthier et al., "Efficacy of Donepezil on Behavioral Symptoms in Patients With Moderate to Severe Alzheimer's Disease," International Psychogeriatrics, 2002, 14(4):389-404.
Grossberg et al., "Memantine Therapy of Behavioral Symptoms in Community-Dwelling Patients with Moderate to Severe Alzheimer's Disease," Dementia and Geriatric Cognitive Disorders, 2009, 27:164-172.
Holmes et al., "The efficacy of donepezil in the treatment of neuropsychiatric symptoms in Alzheimer disease," Neurology, 2004, 63:214-219.
Homma et al., "Clinical Efficacy and Safety of Donepezil on Cognitive and Global Function in Patients with Alzheimer's Disease," Dementia and Geriatric Cognitive Disorders, 2000, 11:299-313.
Homma et al., "Donepezil Treatment of Patients with Severe Alzheimer's Disease in a Japanese Population: Results from a 42-Week, Double-Blind, Placebo-Controlled, Randomized Trial," Dementia and Geriatric Cognitive Disorders, Apr. 2008, 25:399-407.
Horita et al., "Effects of the adenosine $A_{2A}$ antagonist istradefylline on cognitive performance in rats with a 6-OHDA lesion in prefrontal cortex," Psychopharmacology, Dec. 2013, 230(3):345-352.
Howard et al., "Donepezil and Memantine for Moderate-to-Severe Alzheimer's Disease," The New England Journal of Medicine, 2012, 366:893-903.
Hutson et al., "The selective phosphodiesterase 9 (PDE9) inhibitor PF-04447943 (6-[(3S,4S)-4-methyl-1-(pyrimidin-2-ylmethyl)pyrrolidin-3-yl]-1-(tetrahydro-2H-pyran-4-yl)-1,5-dihydro-4H-pyrazolo[3,4-d]pyrimidin-4-one) enhances synaptic plasticity and cognitive function in rodents," Neuropharmacology, Sep. 2011, 61(4):665-676.
International Preliminary Report on Patentability in International Application No. PCT/JP2012/075748, dated Apr. 17, 2014, 10 pages.
International Preliminary Report on Patentability in International Application No. PCT/JP2014/059852, dated Oct. 15, 2015, 8 pages.
International Preliminary Report on Patentability in International Application No. PCT/JP2014/059853, dated Oct. 15, 2015, 7 pages.
International Search Report in International Application No. PCT/JP2012/075748, dated Nov. 20, 2012, 8 pages (with English Translation).
International Search Report in International Application No. PCT/JP2018/020638, dated Aug. 21, 2018, 4 pages (with English Translation).
International Search Report in International Application No. PCT/JP2018/020649, dated Aug. 21, 2018, 3 pages (with English Translation).
International Search Report in International Application No. PCT/JP2018/020650, dated Aug. 21, 2018, 4 pages (with English Translation).
Japanese Society of Neurology [Online], "Dementia with Lewy bodies (included Parkinson's disease)," Chapter 7, Online Dementia disease treatment guidelines, 2010, [Retrieved on Jul. 3, 2018], Retrieved from: URL<http://www.neurology-jp.org.guidelinem/degl/sinkei_degl_2010_08.pdf>, pp. 300-302 (with Partial Translation).
Kleiman et al., "Phosphodiesterase 9A Regulates Central cGMP and Modulates Responses to Cholinergic and Monoaminergic Perturbation in Vivo," J Pharmacol. Exp. Thera., Feb. 9, 2012, 341(2):396-409.

(56) References Cited

OTHER PUBLICATIONS

Lopez et al., "Long-term effects of the concomitant use of memantine with cholinesterase inhibition in Alzheimer disease," J Neurol Neurosurg Psychiatiy, 2009, 80(6):600-607.
McKeith et al., "Diagnosis and management of dementia with Lewy bodies: third report of the DLB Consortium," Neurology, Dec. 2005, 65(12):1863-1872.
McKeith et al., "Efficacy of rivastigmine in dementia with Lewy bodies: a randomised, double-blind, placebo-controlled international study," The Lancet, Dec. 2000, 356(9247):2031-2036.
Mecocci et al., "Effects of memantine on cognition in patients with moderate to severe Alzheimer's disease: post-hoc analyses of ADAS-cog and SIB total and single-item scores from six randomized, double-blind, placebo-controlled studies," International Journal of Geriatric Psychiatry, 2009, 24:532-538.
Mori et al., "Donepezil for Dementia with Lewy Bodies: A Randomized, Placebo-Controlled Trial," Annals of Neurology, 2012, 72:41-52.
Neurology-jp.org [online], "Dementia with Lewy bodies included Parkinson's disease," 2010, [Retrieved on Jan. 16, 2020], retrieved from: URL<http://www.neurology-jp.org/guidelinem/degl/sinkei_degl_2010_08.pdf>, pp. 300-302 (with English Translation).
Notice of Allowance in Australian Patent Application No. 2012319549, dated Jul. 19, 2016, 3 pages.
Notice of Allowance in Israeli Patent Application No. 231650, dated Feb. 10, 2016, 5 pages, (with English Translation).
Notice of Allowance in Japanese Patent Application No. P2013-537544, dated Apr. 30, 2014, 6 pages, (with English Translation).
Notice of Allowance in Russian Patent Application No. 2014112931, dated Aug. 22, 2016, 19 pages, (with English translation).
Notice of Allowance in Singaporean Patent Application No. 11201400717Q, dated May 26, 2016, 4 pages.
Notice of Allowance in South African Patent Application No. 2014/02439, dated Jan. 21, 2015, 3 pages.
Notice of Allowance in Taiwanese Patent Application No. 101136747, dated Aug. 17, 2016, 5 pages, (with English Translation).
Notice of Allowance in U.S. Appl. No. 13/644,745, dated Jun. 10, 2013, 13 pages.
Office Action in Australian Patent Application No. 2012319549, dated Jun. 1, 2016, 7 pages.
Office Action in Chilean Patent Application No. 2014-00821, dated Oct. 29, 2015, 11 pages, (with English Translation).
Office Action in Chinese Patent Application No. 201280046653.2, dated Feb. 28, 2015, 10 pages, (with English Translation).
Office Action in Chinese Patent Application No. 201480016592.4, dated May 12, 2016, 12 pages, (with English Translation).
Office Action in Chinese Patent Application No. 201480016592.4, dated Oct. 16, 2015, 2 pages, (with English Translation).
Office Action in Chinese Patent Application No. 201480017423.2, dated Mar. 1, 2016, 10 pages, (with English Translation).
Office Action in Colombian Patent Application No. 14-059034, dated Mar. 10, 2015, 13 pages, (with English translation).
Office Action in Filipino Patent Application No. 1-2014-500580, dated Jun. 17, 2016, 3 pages.
Office Action in Golf Cooperation Council Patent Application No. GC2012-22447, dated Apr. 21, 2016, 4 pages.
Office Action in Israeli Patent Application No. 231650, dated Jul. 16, 2014, 4 pages, (with English Translation).
Office Action in Israeli Patent Application No. 241695, dated Jan. 24, 2016, 5 pages, (with English Translation).
Office Action in Israeli Patent Application No. 241796, dated Jan. 24, 2016, 5 pages, (with English Translation).
Office Action in Japanese Patent Application No. P2014-538559, dated Sep. 30, 2014, 4 pages, (with English Translation).
Office Action in New Zealand Patent Application No. 622594, dated Feb. 4, 2015, 2 pages.
Office Action in Pakistani Patent Application No. 672/2012, dated Feb. 14, 2013, 8 pages.
Office Action in Taiwanese Patent Application No. 101136747, dated Apr. 22, 2016, 5 pages, (with English Translation).
Office Action in U.S. Appl. No. 13/644,745, dated Mar. 26, 2013, 8 pages.
Office Action in Vietnamese Patent Application No. 1-2015-03459, dated Nov. 25, 2015, 2 pages, (with English Translation).
"PF-04447943: A Phase 2 Controlled Clinical Trial of a Selective PDE9A Inhibitor in Alzheimer's Disease, Apr. 6, 2005," Abstract of Alzheimer's Association International Conference (AAIC) 2011, Jul. 16-21, 2011; Pair, France, 1 page.
Perry et al., "Neocortical cholinergic activities differentiate Lewy body dementia from classical Alzheimer's disease," Neuroreport, Mar. 1994, 5(7):747-749.
Raskind et al., "Galantamine in AD: A 6-month randomized, placebo-controlled trial with a 6-month extension," Neurology, 2000, 54:2261-2268.
Response filed in Chilean Office Action in Application No. 2014-00821, dated Aug. 19, 2015, 26 pages, (with English Translation).
Response filed in Chilean Office Action in Application No. 2014-00821, dated Dec. 16, 2015, 6 pages, (with English Translation).
Response to Examination Report in Australian Patent Application No. 2012319549, dated Jul. 8, 2016, 6 pages.
Response to Extended European Search Report in European Patent Application No. 12837953.4, dated May 15, 2015, 22 pages.
Response to Office Action filed in Chinese Patent Application No. 201280046653.2, dated Apr. 28, 2015, 16 pages, (with English Translation).
Response to Office Action filed in Colombian Patent Application No. 14-059034, dated Jul. 16, 2015, 23 pages, (with English translation).
Response to Office Action in Israeli Patent Application No. 231650, dated Nov. 6, 2014, 8 pages, (with English Translation).
Response to Office Action in Israeli Patent Application No. 241695, dated May 23, 2016, 4 pages (with English Translation).
Response to Office Action in Israeli Patent Application No. 241796, dated May 23, 2016, 4 pages, (with English Translation).
Response to Office Action in New Zealand Patent Application No. 622594, dated May 22, 2015, 16 pages.
Response to Office Action in Russian Patent Application No. 2014112931, dated Jul. 26, 2016, 23 pages, (with English Translation).
Response to Office Action in Vietnamese Patent Application No. 1-2015-03459, dated Dec. 17, 2015, 21 pages, (with English translation).
Sambeth et al., "Cholinergic drugs affect novel object recognition in rats: Relation with hippocampal EEG?," European Journal of Pharmacology, Oct. 2007, 572(2-3):151-159.
Shimada et al., "Mapping of brain acetylcholinesterase alterations in Lewy body disease by PET," Neurology, Jul. 2009, 73(4):273-278.
Singapore Request to Amend Application Before Grant in Application No. 11201400717Q, dated Feb. 12, 2016, 9 pages.
Snyder et al., "Reversal of scopolamine-induced deficits with a single dose of donepezil, an acetylcholinesterase inhibitor," Alzheimer's & Dementia, Oct. 2005, 1(2):126-135.
Submission Document in Filipino Patent Application No. 1-2014-500580, dated Aug. 30, 2016, 3 pages.
Submission Document in Filipino Patent Application No. 1-2014-500580, dated Jul. 21, 2016, 5 pages.
Submission Document in Gulf Cooperation Council Patent Application No. GC2012-22447, dated Jul. 18, 2016, 4 pages, (with English Translation).
Submission Document in Malaysian Patent Application No. PI2014700702, dated Sep. 28, 2016, 12 pages, (with English Translation).
Submission Document in Pakistani Patent Application No. 672/2012, dated Jul. 28, 2016, 17 pages, (with English Translation).
Submission Document in Taiwanese Patent Application No. 101136747, dated Jul. 21, 2016, 15 pages, (with English Translation).
Submission Document in Thai Patent Application No. 1401001864, dated Feb. 15, 2016, 352 pages, (with English Translation).
Submission Documents in Chinese Patent Application No. 2014/80017423.2, dated Jul. 4, 2016, 6 pages, (with English Translation).

(56) References Cited

OTHER PUBLICATIONS

Takano et al., "Oral Absorption of Poorly Water-Soluble Drugs: Computer Simulation of Fraction Absorbed in Humans From a Miniscale Dissolution Test," Pharm Res, Jun. 2006, 23(6):1144-1156.
Tiraboschi et al., "Cholinergic dysfunction in diseases with Lewy bodies," Neurology, Jan. 2000, 54(2):407-411.
Winblad et al., "IDEAL: A 6-month, double-blind, placebo-controlled study of the first skin patch for Alzheimer disease," Neurology, 2007, 69(Suppl. 1):69:S14-S22.
Ando et al., "Preclinical Characterization of E2027, A novel Phosphodiesterase 9 Inhibitor," Alzheimer's & Dementia: The Journal of the Alzheimer's Association, Jul. 2017, 13(7):p946, XP085217616, 1 page.
Chin et al., "Donepezil in the one-year treatment of dementia with Lewy bodies and Alzheimer's disease," Journal of Neurological Sciences, 2017, 381:p322, XP085294732, 1 page.
Magierski et al., "1.206—Donepezil versus rivastigmine tolerability study in dementia with Lewy bodies and Alzheimer's disease," Parkinsonism and Related Disorders, Elsevier Science, Oxford, GB, 2007, 13:S62, XP022635787, 1 page.
Notice of Allowance in U.S. Appl. No. 16/607,402, dated Jan. 13, 2021, 23 pages.
Notice of Allowance in U.S. Appl. No. 16/607,459, dated Feb. 3, 2021, 4 pages.
Notice of Allowance in U.S. Appl. No. 16/607,459, dated Jan. 14, 2021, 23 pages.
Office Action in Egyptian Patent Application No. PCT529/2014, dated Dec. 7, 2020, 12 pages (with English Translation).
Office Action in Mexican Patent Application No. MX/a/2019/013198, dated Oct. 5, 2020, 7 pages (with English Translation).
Search Report in European Patent Application No. 18808870.2, dated Feb. 17, 2021, 4 pages.
Search Report in European Patent Application No. 18809656.4, dated Jan. 22, 2021, 7 pages.
Search Report in European Patent Application No. 18810202.4, dated Nov. 23, 2020, 9 pages.
Search Report in European Patent Application No. 18810578.7, dated Jan. 20, 2021, 6 pages.
Submission Document in Israeli Patent Application No. 270318, dated Nov. 16, 2020, 55 pages (with English Translation).
Submission Document in Israeli Patent Application No. 270357, dated Dec. 7, 2020, 5 pages (with English Translation).
Submission Document in Israeli Patent Application No. 270394, dated Nov. 15, 2020, 40 pages (with English Translation).
Submission Document in Israeli Patent Application No. 270395, dated Nov. 17, 2020, 35 pages (with English Translation).
Submission Document in Mexican Patent Application No. MX/a/2019/013198, dated Dec. 2, 2020, 12 pages (with English Translation).
Notice of Allowance in Russian Patent Application No. 2015140619, dated Apr. 20, 2021, 12 pages (with English Translation).
Notice of Allowance in Vietnamese Patent Application No. 1-2014-01049, dated Jul. 31, 2017, 2 pages (with English Translation).
Office Action in Argentine Patent Application No. P120103702, dated Aug. 16, 2019, 4 pages (with English Translation).
Office Action in Brazilian Patent Application No. BR112014007912-9, dated Jul. 2, 2019, 10 pages (with English Translation).
Office Action in Brazilian Patent Application No. BR112015024393-2, dated Oct. 22, 2019, 10 pages (with English Translation).
Office Action in Mexican Patent Application No. MX/a/2019/013198, dated Mar. 18, 2021, 8 pages (with English Translation).
Office Action in Peruvian Patent Application No. 000408-2014, dated Mar. 12, 2018, 13 pages (with English Translation).
Office Action in Russian Patent Application No. 2015140619, dated Mar. 26, 2018, 12 pages (with English Translation).
Office Action in Vietnamese Patent Application No. 1-2014-01049, dated May 15, 2014, 2 pages (with English Translation).
Office Action in Vietnamese Patent Application No. 1-2014-01049, dated May 16, 2017, 2 pages (with English Translation).
Submission Document in Argentine Patent Application No. P120103702, dated Oct. 24, 2019, 10 pages (with English Translation).
Submission Document in Brazilian Patent Application No. BR112014007912-9, dated Aug. 26, 2019, 12 pages (with English Translation).
Submission Document in Brazilian Patent Application No. BR112015024393-2, dated Jan. 17, 2020, 18 pages (with English Translation).
Submission Document in Peruvian Patent Application No. 000408-2014, dated Apr. 10, 2018, 14 pages (with English Translation).
Submission Document in Russian Patent Application No. 2015140619, dated Apr. 10, 2018, 12 pages (with English Translation).
Submission Document in Vietnamese Patent Application No. 1-2014-01049, dated Jun. 12, 2014, 19 pages (with English Translation).
Submission Document in Vietnamese Patent Application No. 1-2014-01049, dated Jun. 8, 2017, 11 pages (with English Translation).
Official Notification in U.S. Appl. No. 16/607,402, dated Mar. 9, 2021, 2 pages.
Official Notification in U.S. Appl. No. 16/607,459, dated Mar. 2, 2021, 2 pages.
Submission Document in Egyptian Patent Application No. PCT529/2014, dated Mar. 4, 2021, 12 pages (with English Translation).
Submission Document in U.S. Appl. No. 16/607,402, dated Feb. 23, 2021, 17 pages.
Submission Document in U.S. Appl. No. 16/607,459, dated Feb. 23, 2021, 18 pages.
[No Author Listed], "Eisai Scientific Meeting 2019," Presentation, Eisai Co., Ltd., Apr. 23, 2019, 137 pages.
Ando et al., "Effects of repeated administration of E2027, a novel phosphodiesterase-9 inhibitor, on cyclic GMP levels in rat cerebrospinal fluid," Poster presented at Alzheimer's Association International Conference (AAIC), Chicago, IL, Jul. 22-26, 2018, p. 3-062, 1 page.
Ando et al., "Preclinical characterization of E2027, a novel phosphodiesterase (PDE) 9 inhibitor," Poster presented at Alzheimer's Association International Conference (AAIC), Jul. 16-20, 2017, p. 3-043, 1 page.
Goto et al., "Effect of E2027, a Novel Phosphodiesterase-9 Inhibitor, on Cognitive Function and Hippocampal Cyclic GMP in Tg2576 Mouse Model of Alzheimer's Disease," Poster presented at 15th International Conference on Alzheimer's & Parkinson Disease (AD/PD), Virtual Conference, Mar. 9-14, 2021, p. 153, 1 page.
Lai et al., "Phase 1 Investigation into the Safety, Tolerability, Pharmacokinetics (PK) and Pharmacodynamics (PD) of E2027, a Selective Phosphodiesterase-9 (PDE9) Inhibitor," Presentation slides presented at Alzheimer's Association International Conference (AAIC), Jul. 16-20, 2017, pp. 1-10.
Landry et al., "Concentration Response Modeling of ECG Data for E2027 to Inform Dose Selection for Phase 2 Dementia in Lewy Body Study," Poster presented at 14th International Conference on Alzheimer's & Parkinson's Diseases, (AD/PD 2019), Lisbon, Portugal, Mar. 26-31, 2019, 1 page.
Landry et al., "E2027, a novel phosphodiesterase-9 (PDE9) inhibitor in development for treatment of dementia with Lewy bodies (DLB), showed no clinically significant drug interaction with diltiazem," Poster presented at Alzheimer's Association International Conference (AAIC), Chicago, IL, Jul. 22-26, 2018, p. 1-055, 1 page.
Landry et al., "Phase 1 Multiple Ascending Dose (MAD) Study of Phosphodiesterase-9 Inhibitor E2027: Confirmation of Target Engagement and Selection of Phase 2 Dose in Dementia with Lewy Bodies," Presentation slides presented at Alzheimer's Association International Conference (AAIC), Jul. 22-26, 2018, pp. 1-10.
Notice of Allowance in Australian Patent Application No. 2014250392, dated Feb. 14, 2018, 3 pages.
Notice of Allowance in Canadian Patent Application No. 2861795, dated Sep. 7, 2018, 1 page (with English Translation).
Notice of Allowance in Canadian Patent Application No. 2907971, dated Sep. 1, 2020, 1 page (with English Translation).
Notice of Allowance in Chinese Patent Application No. 201280046653.2, dated Jun. 23, 2015, 4 pages (with English Translation).
Notice of Allowance in Chinese Patent Application No. 201480017423.2, dated Mar. 20, 2017, 4 pages (with English Translation).

(56) References Cited

OTHER PUBLICATIONS

Notice of Allowance in Colombian Patent Application No. 14-059034, dated Aug. 18, 2015, 6 pages (with English Translation).
Notice of Allowance in European Patent Application No. 12837953.4, dated Aug. 26, 2015, 156 pages.
Notice of Allowance in European Patent Application No. 14780139.3, dated Apr. 6, 2017, 62 pages.
Notice of Allowance in Indonesian Patent Application No. P00201401905, dated Mar. 25, 2019, 5 pages (with English Translation).
Notice of Allowance in Korean Patent Application No. 10-2014-7008769, dated Dec. 3, 2018, 4 pages (with English Translation).
Notice of Allowance in Korean Patent Application No. 10-2015-7026005, dated May 1, 2019, 6 pages (with English Translation).
Notice of Allowance in Mexican Patent Application No. MX/a/2014/003800, dated Jun. 22, 2018, 4 pages (with English Translation).
Notice of Allowance in Mexican Patent Application No. MX/a/2015/013620, dated Sep. 18, 2018, 5 pages (with English Translation).
Notice of Allowance in Pakistani Patent Application No. 458/2016, dated Mar. 19, 2020, 1 page.
Notice of Allowance in Pakistani Patent Application No. 672/2012, dated Mar. 19, 2020, 1 page.
Notice of Allowance in Singaporean Patent Application No. 11201507897S, dated Oct. 27, 2017, 5 pages.
Notice of Allowance in Thai Patent Application No. 1401001864, dated Sep. 26, 2019, 2 pages (with English Translation).
Notice of Allowance in U.S. Appl. No. 14/778,695, dated Nov. 4, 2016, 9 pages.
Office Action in Canadian Patent Application No. 2861795, dated May 30, 2018, 3 pages.
Office Action in Canadian Patent Application No. 2907971, dated Apr. 28, 2020, 5 pages.
Office Action in Indian Patent Application No. 2463/CHENP/2014, dated Jun. 11, 2018, 6 pages (with English Translation).
Office Action in Indian Patent Application No. 5808/CHENP/2015, dated Oct. 26, 2018, 5 pages (with English Translation).
Office Action in Indian Patent Application No. 5808/CHENP/2015, dated May 28, 2019, 2 pages (with English Translation).
Office Action in Indonesian Patent Application No. P00201401905, dated Nov. 26, 2018, 5 pages (with English Translation).
Office Action in Israeli Patent Application No. 241796, dated Feb. 14, 2018, 8 pages (with English Translation).
Office Action in Korean Patent Application No. 10-2014-7008769, dated Sep. 3, 2018, 8 pages (with English Translation).
Office Action in Korean Patent Application No. 10-2015-7026005, dated Jan. 2, 2019, 10 pages (with English Translation).
Office Action in Malaysian Patent Application No. PI2014700702, dated Jun. 29, 2018, 3 pages.
Office Action in Mexican Patent Application No. MX/a/2014/003800, dated Jan. 15, 2018, 9 pages (with English Translation).
Office Action in Mexican Patent Application No. MX/a/2015/013620, dated May 22, 2018, 13 pages (with English Translation).
Office Action in Pakistani Patent Application No. 458/2016, dated Apr. 6, 2018, 2 pages.
Schuck et al., "Population pharmacokinetic-pharmacodynamic (PPK/PD) modeling of E2027, a selective phosphodiesterase-9 (PDE9) inhibitor, following single ascending oral doses in healthy volunteers," Poster presented at Alzheimer's Association International Conference (AAIC), Jul. 16-20, 2017, p. 1-056, 1 page.
Submission Document in Canadian Patent Application No. 2861795, dated Jul. 17, 2018, 12 pages.
Submission Document in Canadian Patent Application No. 2907971, dated Jun. 26, 2020, 12 pages.
Submission Document in Indian Patent Application No. 2463/CHENP/2014, dated Nov. 30, 2018, 10 pages.
Submission Document in Indian Patent Application No. 5808/CHENP/2015, dated Jan. 16, 2019, 6 pages.
Submission Document in Indian Patent Application No. 5808/CHENP/2015, dated Jul. 2, 2019, 88 pages.
Submission Document in Indonesian Patent Application No. P00201401905, dated Feb. 22, 2019, 7 pages (with English Translation).
Submission Document in Israeli Patent Application No. 241796, dated Jun. 3, 2018, 3 pages (with English Translation).
Submission Document in Korean Patent Application No. 10-2014-7008769, dated Oct. 1, 2018, 11 pages (with English Translation).
Submission Document in Korean Patent Application No. 10-2015-7026005, dated Feb. 14, 2019, 23 pages (with English Translation).
Submission Document in Mexican Patent Application No. MX/a/2014/003 800, dated Feb. 16, 2018, 4 pages (with English Translation).
Submission Document in Mexican Patent Application No. MX/a/2015/013620, dated Jun. 25, 2018, 8 pages (with English Translation).
Submission Document in Pakistani Patent Application No. 458/2016, dated Jul. 2, 2018, 3 pages.
Submission Document in Pakistani Patent Application No. 458/2016, dated May 29, 2020, 8 pages.
Notice of Allowance in U.S. Appl. No. 16/607,402, dated Dec. 15, 2021, 4 pages.
Notice of Allowance in U.S. Appl. No. 16/611,374, dated Dec. 1, 2021, 8 pages.
Submission Document in U.S. Appl. No. 16/607,402, dated Dec. 9, 2021, 13 pages.
Notice of Allowance in U.S. Appl. No. 16/607,402, dated Dec. 1, 2021, 4 pages.
Office Action in Mexican Patent Application No. MX/a/2019/013398, dated Nov. 29, 2021, 11 pages (with English Translation).
Office Action in Mexican Patent Application No. MX/a/2019/013198, dated Nov. 4, 2021, 9 pages (with English Translation).
Office Action in Russian Patent Application No. 2019135834, dated Oct. 15, 2021, 11 pages (with English Translation).
Notice of Allowance in U.S. Appl. No. 16/607,402, dated May 5, 2021, 8 pages.
Notice of Allowance in U.S. Appl. No. 16/607,402, dated Aug. 19, 2021, 10 pages.
Notice of Allowance in U.S. Appl. No. 16/607,402, dated Sep. 1, 2021, 7 pages.
Notice of Allowance in U.S. Appl. No. 16/607,402, dated Oct. 8, 2021, 4 pages.
Notice of Allowance in U.S. Appl. No. 16/607,459, dated May 18, 2021, 15 pages.
Notice of Allowance in U.S. Appl. No. 16/607,459, dated Jul. 30, 2021, 5 pages.
Notice of Allowance in U.S. Appl. No. 16/607,459, dated Aug. 19, 2021, 5 pages.
Notice of Allowance in U.S. Appl. No. 16/607,459, dated Sep. 10, 2021, 4 pages.
Office Action in Argentine Patent Application No. P120103702, dated Apr. 20, 2021, 11 pages (with English Translation).
Office Action in Australian Patent Application No. 2018278422, dated Jul. 7, 2021, 3 pages.
Office Action in Brazilian Patent Application No. BR112014007912-9, dated Oct. 26, 2021, 8 pages (with English Translation).
Office Action in Egyptian Patent Application No. PCT529/2014, dated Aug. 15, 2021, 12 pages (with English Translation).
Office Action in European Patent Application No. 18810202.4, dated Nov. 15, 2021, 7 pages.
Office Action in Indian Patent Application No. 201947044330, dated Jun. 14, 2021, 5 pages (with English Translation).
Office Action in Indian Patent Application No. 201947044352, dated Jun. 25, 2021, 6 pages (with English Translation).
Office Action in Indian Patent Application No. 201947044546, dated May 5, 2021, 5 pages (with English Translation).
Office Action in Indian Patent Application No. 201947044589, dated Jun. 29, 2021, 6 pages (with English Translation).
Office Action in Mexican Patent Application No. MX/a/2019/013383, dated Aug. 17, 2021, 8 pages (with English Translation).
Office Action in Mexican Patent Application No. MX/a/2019/013397, dated Aug. 31, 2021, 12 pages (with English Translation).

(56) References Cited

OTHER PUBLICATIONS

Office Action in Russian Patent Application No. 2019135261, dated Sep. 8, 2021, 15 pages (with English Translation).
Office Action in Russian Patent Application No. 2019135690, dated Aug. 25, 2021, 24 pages (with English Translation).
Office Action in Russian Patent Application No. 2019135838, dated Sep. 29, 2021, 10 pages (with English Translation).
Office Action in U.S. Appl. No. 16/611,374, dated May 12, 2021, 34 pages.
Submission Document in Argentine Patent Application No. P120103702, dated Jul. 5, 2021, 357 pages (with English Translation).
Submission Document in Egyptian Patent Application No. PCT529/2014, dated Nov. 3, 2021, 11 pages (with English Translation).
Submission Document in European Patent Application No. 18808870.2, dated Sep. 9, 2021, 9 pages.
Submission Document in European Patent Application No. 18809656.4, dated Aug. 19, 2021, 9 pages.
Submission Document in European Patent Application No. 18810202.4, dated Jun. 14, 2021, 23 pages.
Submission Document in European Patent Application No. 18810578.7, dated Aug. 16, 2021, 13 pages.
Submission Document in Mexican Patent Application No. MX/a/2019/013198, dated Jul. 21, 2021, 11 pages (with English Translation).
Submission Document in U.S. Appl. No. 16/607,402, dated Jul. 16, 2021, 15 pages.
Submission Document in U.S. Appl. No. 16/607,459, dated Aug. 13, 2021, 12 pages.
Submission Document in U.S. Appl. No. 16/607,459, dated Sep. 3, 2021, 13 pages.
Submission Document in U.S. Appl. No. 16/607,459, dated Sep. 16, 2021, 9 pages.
Tandfonline.com [online], Vardigan et al., "The Selective Phosphodiesterase 9 (PDE9) Inhibitor PF-04447943 Attenuates a Scopolamine-Induced Deficit in a Novel Rodent Attention Task," Abstract, Journal of Neurogenetics, Nov. 2011, 25(4), [Retrieved on May 7, 2021], retrieved from: URL<https://doi.org/10.3109/01677063.2011.630494>, 2 pages.
Submission Document in Brazilian Patent Application No. BR112014007912-9, dated Jan. 21, 2022, 10 pages (with English Translation).
Office Action in Taiwanese Patent Application No. 107118423, dated Dec. 23, 2021, 9 pages (with English Translation).
Submission Document in Mexican Patent Application No. MX/a/2019/013383, dated Dec. 15, 2021, 16 pages (with English Translation).
Notice of Allowance in U.S. Appl. No. 16/607,402, dated Feb. 28, 2022, 4 pages.
Office Action in Indian Patent Application No. 201947044330, dated Mar. 29, 2022, 2 pages (with English Translation).
Office Action in Mexican Patent Application No. MX/a/2019/013198, dated Mar. 16, 2022, 11 pages (with English Translation).
Office Action in Mexican Patent Application No. MX/a/2019/013383, dated Jan. 12, 2022, 8 pages (with English Translation).
Office Action in Mexican Patent Application No. MX/a/2019/013397, dated Feb. 2, 2022, 15 pages (with English Translation).
Submission Document in Indian Patent Application No. 201947044330, dated Mar. 10, 2022, 8 pages.
Submission Document in Indian Patent Application No. 201947044589, dated Mar. 29, 2022, 16 pages.
Submission Document in Mexican Patent Application No. MX/a/2019/013397, dated Jan. 13, 2022, 9 pages (with English Translation).
Submission Document in Mexican Patent Application No. MX/a/2019/013198, dated Mar. 4, 2022, 10 pages (with English Translation).
Office Action in Indian Patent Application No. 201947044330, dated Apr. 12, 2022, 2 pages (with English Translation).
Office Action in Japanese Patent Application No. P2019-559117, dated Jun. 7, 2022, 6 pages (with English Translation).
Notice of Allowance in Japanese Patent Application No. P2019-521248, dated Apr. 26, 2022, 7 pages (with English Translation).
Office Action in Chinese Patent Application No. 201880030146.7, dated Apr. 15, 2022, 12 pages (with English Translation).
Office Action in Egyptian Patent Application No. PCT529/2014, dated Mar. 17, 2022, 12 pages (with English Translation).
Office Action in Israeli Patent Application No. 270318, dated Apr. 13, 2022, 4 pages.
Office Action in Japanese Patent Application No. P2019-521251, dated Apr. 26, 2022, 6 pages (with English Translation).
Submission Document in European Patent Application No. 18810202.4, dated May 24, 2022, 4 pages.
Submission Document in Indian Patent Application No. 201947044330, dated May 27, 2022, 12 pages.
Submission Document in Mexican Patent Application No. MX/a/2019/013198, dated Jul. 15, 2022, 8 pages (with English Translation).
Submission Document in Russian Patent Application No. 2019135261, dated Aug. 3, 2022, 14 pages (with English Translation).
Landry et al., "O1-12-06: Phase 1 Multiple Ascending Dose (MAD) Study of Phosphodiesterase-9 Inhibitor E2027: Confirmation of Target Engagement and Selection of Phase 2 Dose in Dementia With Lewy Bodies," Alzheimer's & Dementia, 2006, 14(7S_Part_4), p. 251.
Office Action in Chinese Patent Application No. 201880027744.9, dated Jun. 28, 2022, 15 pages (with English Translation).
Office Action in Russian Patent Application No. 2019135261, dated Sep. 13, 2022, 13 pages (with English Translation).
Submission Document in Chinese Patent Application No. 201880027744.9, dated Sep. 7, 2022, 207 pages (with English Translation).

\* cited by examiner

PHARMACEUTICAL COMPOSITION COMPRISING PDE9 INHIBITOR

TECHNICAL FIELD

The present invention is directed to pharmaceutical compositions comprising a PDE9 inhibitor.

BACKGROUND ART

Cyclic guanosine monophosphate (hereinafter, referred to as cGMP) functioning as a second messenger in cells is known to play an important role in various physiological functions including learning and memory behaviors.

On the postsynaptic site of the brain neural circuits, nitrogen monoxide (hereinafter, referred to as NO) biosynthesized by a nitrogen monoxide synthetase activates a guanylate cyclase, which is a cGMP synthetase. The activated guanylate cyclase biosynthesizes cGMP from guanosine triphosphate. The cGMP activates a cGMP-dependent protein kinase (hereinafter, referred to as PKG) to phosphorylate various proteins participating in synapse plasticity. The activation of the NO/cGMP/PKG cascade is known to participate in the induction of synapse plasticity (Long Term Potentiation; hereinafter, referred to as LTP) of the hippocampus known as a neural substrate for learning and memory behaviors (for example, see Domek-Lopacinska et al., "Cyclic GMP metabolism and its role in brain physiology", J Physiol Pharmacol., vol. 56, Suppl 2: pp. 15-34, 2005). A medicine activating the signal transmission of the cascade is known to improve LTP of the hippocampus and the learning behavior of animals, while a medicine inhibiting the cascade is known to exhibit the opposite action (Wang X., "Cyclic GMP-dependent protein kinase and cellular signaling in the nervous system", J. Neurochem., vol. 68, pp. 443-456, 1997). Therefore, from these findings, an increase in cGMP in the brain is anticipated to lead to an improvement of learning and memory behaviors.

cGMP is metabolized to 5'-GMP having no PKG activation action by a phosphodiesterase (hereinafter, referred to as PDE). The PDE is known to have 11 families, and PDE9 is known to metabolize specifically cGMP, and to be expressed in the brain, the spleen, the small intestine and the like (for example, see Fisher et al., "Isolation and characterization of PDE9A, a novel human cGMP-specific phosphodiesterase", J. Biol. Chem., vol. 273: pp. 15559-15564, 1998). That is, inhibition of PDE9 is anticipated to increase cGMP in brains. It is reported that a PDE9 inhibitor actually enhances hippocampus LTP, and improves the learning and memory behaviors in a novel-object recognition test/passive avoidance learning test or the like in animals (van der Stsay et al., "The novel selective PDE9 inhibitor BAY 73-6691 improves learning and memory in rodents", Neuropharmacology, vol. 55: pp. 908-918, 2008). Clinically, guanylate cyclase activity decreases and possibility of a decrease in the cGMP level is indicated in the superior temporal cortex of Alzheimer's disease patients, (Bonkale et al., "Reduced nitric oxide responsive soluble guanylyl cyclase activity in the superior temporal cortex of patients with Alzheimer's disease", Neurosci. Lett., vol 187, pp. 5-8, 1995). Therefore, the PDE9 has a possibility of having many close relations with pathologies of neurodegenerative diseases and psychiatric diseases, particularly with pathologies of cognitive dysfunctions and the like in the Alzheimer's disease, such as Alexander's disease, Alpers' disease, Alzheimer's disease, amyotrophic lateral sclerosis (ALS; known as Lou Gehrig's disease or motor neuron disease), ataxia-telangiectasia, Batten's disease (known also as Spielmeyer-Vogt-Sjogren-Batten's disease), Binswanger's dementia (subcortical angiosclerotic encephalopathy), bipolar disorder, bovine spongiform encephalopathy (BSE), Canavan's disease, chemotherapy induction dementia, Cockayne's syndrome, corticobasal degeneration, Creutzfeldt-Jakob's disease, depression, Down's syndrome, frontotemporal lobe degeneration (including frontotemporal dementia, semantic dementia and progressive nonfluent aphasia), Gerstmann-Straussler-Scheinker's disease, glaucoma, Huntington's disease (chorea), HIV related dementia, hyperkinesis, Kennedy's disease, Korsakoffs syndrome (amnesic confabulation syndrome), Krabbe's disease, Lewy-bodies dementia, progressive logopenic aphasia, Machado-Joseph's disease (spinocerebellar ataxia type 3), multiple sclerosis, multiple atrophy (olivopontocerebellar atrophy), myasthenia gravis, Parkinson's disease, Pelizaeus-Merzbacher's disease, Pick's disease, dementia presenilis (slight cognitive impairment), primary lateral sclerosis, primary progressive aphasia, radiation-induced dementia, Refsum's disease (phytanic acid storage disease), Sandhof's disease, Schilder's disease, schizophrenia, semantic dementia, senile dementia, Shy-Drager syndrome, spinocerebellar ataxia, spinal muscle atrophy, Steele-Richardson-Olszewski's disease (progressive supranuclear palsy), and vascular amyloidosis and vascular dementia (multiple infarct dementia).

(S)-7-(2-methoxy-3,5-dimethylpyridin-4-yl)-1-(tetrahydrofuran-3-yl)-1H-pyrazolo[4,3-c] quin olin-4(5H)-one represented by Formula (1) (to be simply referred to as "Compound A") is known to have a PDE9 inhibitory activity. Compound A or pharmaceutically acceptable salts thereof is expected to be used for treatment of neurodegenerative diseases or psychiatric diseases (WO2013/051369, WO2014/163147).

[Chem. 1]

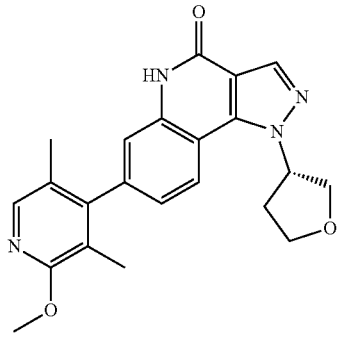

Formula (1)

However, the relationship between the pharmacokinetics (hereinafter referred to as "PK") of Compound A in human subjects, the therapeutically effective amount thereof to be expected and the results of In Vivo test thereof has not been known.

SUMMARY OF INVENTION

It is an object of the present invention to provide a pharmaceutical composition comprising a therapeutically effective amount of Compound A or pharmaceutically acceptable salts thereof.

The present invention relates to the following <1> to <13>.

<1> An oral dosage form comprising a therapeutically effective amount of Compound A or pharmaceutically acceptable salts thereof and at least one pharmaceutically acceptable excipient, wherein said therapeutically effective amount is single daily dose to achieve a mean Cmax of from about 1.8 ng/mL to about 7.6 ng/mL for each 1 mg of Compound A after administration to human subjects, and said Compound A is (S)-7-(2-methoxy-3,5-dimethylpyridin-4-yl)-1H-(tetrahydrofuran-3-yl)-1H-pyrazolo[4,3-c]quinolin-4(5H)-one represented by Formula (1).

[Chem. 2]

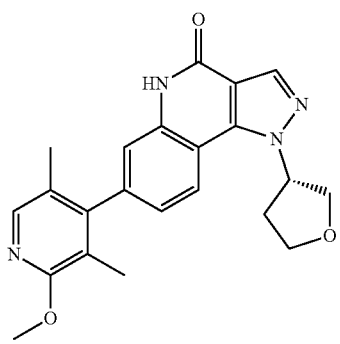

Formula (1)

<2> The oral dosage form of <1>, wherein said single daily dose ranges from about 50 mg to about 400 mg.
<3> The oral dosage form of <1>, wherein said therapeutically effective amount is single daily dose to achieve a mean AUC(0-inf) of from about 72.6 to about 217.0 ng*hr/mL for each 1 mg of Compound A after administration to human subjects.
<4> The oral dosage form of <1>, wherein said therapeutically effective amount is single daily dose to achieve a mean AUC(0-t) of from about 71.0 to about 210.0 ng*hr/mL for each 1 mg of Compound A after administration to human subjects.
<5> An oral dosage form comprising about 25 mg to about 400 mg of Compound A or pharmaceutically acceptable salts thereof and at least one pharmaceutically acceptable excipient, and said Compound A is (S)-7-(2-methoxy-3,5-dimethylpyridin-4-yl)-1H-(tetrahydrofiuran-3-yl)-1H-pyrazolo[4,3-c]quin olin-4(5H)-one represented by Formula (1).

[Chem. 3]

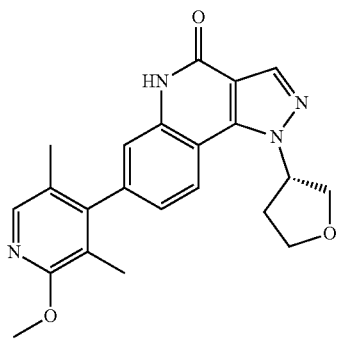

Formula (1)

<6> The oral dosage form of <5>, wherein said Compound A or pharmaceutically acceptable salts thereof at a single daily dose achieves a mean Cmax of from about 1.8 ng/mL to about 7.6 ng/mL for each 1 mg of Compound A after administration to human subjects.
<7> The oral dosage form of <5>, wherein said Compound A or pharmaceutically acceptable salts thereof at a single daily dose achieves a mean AUC(0-inf) of from about 72.6 to about 217.0 ng*hr/mL for each 1 mg of Compound A after administration to human subjects.
<8> The oral dosage form of <5>, wherein said Compound A or pharmaceutically acceptable salts thereof at a single daily dose achieves a mean AUC(0-t) of from about 71.0 to about 210.0 ng*hr/mL for each 1 mg of Compound A after administration to human subjects.
<9> The oral dosage form of <1> or <5>, wherein said oral dosage form is used for treatment of Alzheimer's disease or Lewy body dementia.
<10> A method of treating Alzheimer's disease or Lewy body dementia, comprising administering orally to a human subject in need thereof a dosage form with a therapeutically effective amount of Compound A or pharmaceutically acceptable salts thereof, wherein said therapeutically effective amount is single daily dose to achieve a mean Cmax of from about 1.8 ng/mL to about 7.6 ng/mL for each 1 mg of Compound A after administration to the human subject, and said Compound A is (S)-7-(2-methoxy-3,5-dimethylpyridin-4-yl)-1-(tetrahydrofuan-3-yl)-1H-pyrazolo[44,3-c]quinolin-4(5H)-one represented by Formula (1).

[Chem. 4]

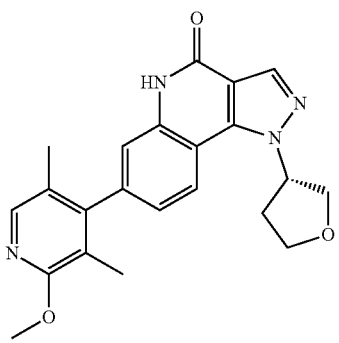

Formula (1)

<11> The method of <10>, wherein said single daily dose ranges from about 25 mg to about 400 mg.
<12> The method of <10>, wherein said therapeutically effective amount is single daily dose to achieve a mean AUC(0-inf) of from about 72.6 to about 217.0 ng*hr/mL for each 1 mg of Compound A after administration to the human subject.
<13> The method of <10>, wherein said therapeutically effective amount is single daily dose to achieve a mean AUC(0-t) of from about 71.0 to about 210.0 ng*hr/mL for each 1 mg of Compound A after administration to the human subject.

DESCRIPTION OF EMBODIMENTS

I. Definitions

In order the invention described herein may be more fully understood, the following definitions are provided for the purposes of the disclosure:

The term "effective amount" means an amount of drug of Compound A that is capable of achieving a therapeutic effect in a human subjective in need thereof.

The term "human subject" shall mean a normal healthy male or female volunteers and/or any individual that presents with clinical signs or symptoms of Alzheimer's disease or Lewy body dementia.

The expression "bioequivalent" or "bioequivalence" is a term of art and is intended to be defined in accordance with Approved Drug Products with Therapeutic Equivalence Evaluations, 34th Edition, which is published by the U.S Department of Health and Human Services, and is commonly known as the "Orange Book". Bioequivalence of different formulation of the same drug substance involves equivalence with respect to the rate and extent of drug absorption. The extent and rate of absorption of the test formulation is compared to a reference formulation in order to determine whether the two formulations are bioequivalent. The standard bioequivalence study is conducted in crossover fashion by extensive testing which includes administering single doses of the test and reference drugs to a number of volunteers, usually 12 to 24 healthy normal adults, and then measuring the blood or plasma levels of the drug over time. Detailed guidelines for establishing the bioequivalence of a formulation with a reference formulation have been published by the FDA Office of Generic Drugs, Division of Bioequivalence.

Two formulations whose PK parameters such as Cmax, AUC, or tmax differ by −20%/+25% or less are generally considered to be "bioequivalent". Another approach for average bioequivalence involves the calculation of a 90% confidence interval for the ratio of the averages (population geometric means) of the measures for the test and reference products. To establish bioequivalence, the calculated confidence interval should fall within usually 80-125% for the ratio of the product averages. In addition to this general approach, the others approach, including (1) logarithmic transformation of pharmacokinetic data, (2) methods to evaluate sequence effects and (3) methods to evaluate outlier data, may be useful for the establishment of bioequivalence. For example, in the above (1) the confidence interval should fall within usually 80-125% for the difference in the mean value of the logarithmic converted PK parameter.

The term "dosage form(s)" shall mean the means to administer the drug substance (active pharmaceutical ingredient (API)), or to facilitate dosing, administration, and delivery of the medicine to the patient and other mammals. Dosage forms are classified in terms of administration routes and application sites, including, for example, oral, topical, rectal, vaginal, intravenous, subcutaneous, intramuscular, ophthalmic, nasal, otic and inhalation administration. Alternatively, dosage forms are classified in terms of physical form such as solid, semi-solid or liquid. Furthermore, dosage forms are subdivided based on their form, functions and characteristics, including, without limited, tablet, capsule or injection as described in monograph of Japanese Pharmacopoeia 16 edition (JP16) or General Chapter <1151> Pharmaceutical Dosage Forms of U.S. Pharmacopoeia-NF (37) (USP37).

The term "excipient" shall mean a typically inactive ingredient used as a vehicle (for example, water, capsule shell etc.), a diluent, or a component to constitute a dosage form or pharmaceutical composition comprising a drug such as a therapeutic agent. The term also encompasses a typically inactive ingredient that imparts cohesive function (i.e. binder), disintegrating function (i.e. disintegrator), lubricant function (lubricating agent), and/or the other function (i.e. solvent, surfactant etc.) to the composition.

The term "a mean" refers to a geometric mean. The pharmacokinetic parameters such as "a mean Cmax" or "a mean AUC" refer to the geometric mean value of a Cmax or an AUC.

If Compound A is in the form of a pharmaceutically acceptable salt, "a mean Cmax for each 1 mg of Compound A" or "a mean AUC for each 1 mg of Compound A" shall mean a mean Cmax or a mean AUC for each 1 mg in terms of free form of Compound A.

If Compound A is in the form of a pharmaceutically acceptable salt, a single daily dose of pharmaceutically acceptable salt of Compound A shall be described as a value in terms of free form of Compound A in this application. In addition, if Compound A is in the form of a pharmaceutically acceptable salt, an amount of pharmaceutically acceptable salt of Compound A contained in an oral dosage form shall be described as a value in terms of free form of Compound A in this application.

The list of the abbreviations and definitions of the terms used in this application is presented the following.

Ae(0-96 h): Cumulative amount of drug excreted in urine up to 96 hours postdose

Amax: Maximum change (%) of cerebrospinal fluid (CSF) cyclic guanosine monophosphate (cGMP) concentration compared to baseline at a single time point within 30 hours postdose AUAC(0-30 h): Area under the concentration-time curve from zero time to 30 hours postdose ΔAUAC(0-30 h): Change (%) in AUAC averaged over 30 hours postdose relative to baseline AUAC averaged over 3 hours predose for CSF cGMP, ie, (AUAC(0-30 h)/30−AUAC(−3-0 h)/3)/(AUAC(−3-0 h)/3)

AUC: Area under the plasma concentration-time curve

AUC(0-24 h): Area under the plasma concentration-time curve from time zero time to 24 hours postdose AUC(0-30 h): Area under the plasma concentration-time curve from time zero time to 30 hours postdose AUC(0-72 h): Area under the plasma concentration-time curve from time zero time to 72 hours postdose AUC(0-t): Area under the plasma concentration-time curve from time zero to time of last quantifiable concentration AUC(0-inf): Area under the plasma concentration-time curve from time zero to infinite time cGMP: Cyclic guanosine monophosphate CL/F: Apparent total clearance following extravascular (eg, oral) administration CLR: Renal clearance Cmax: Maximum observed concentration CSF: Cerebrospinal fluid % CV: sqrt(exp[SD**2 of log-transformed data]−1) *100

Fe(0-96 h): Fraction of dose excreted in urine up to 96 hours postdose

GM: Geometric mean

QTcF: QT interval corrected using Fridericia's formula

ΔQTcF: Mean change-from-baseline QTcF

ΔΔQTcF: Placebo-corrected ΔQTcF

SD: Standard deviation

TAmax: Time at which Amax occurs for CSF cGMP t1/2: Terminal elimination half-life tlag: Absorption lag time tmax: Time to reach maximum (peak) concentration following drug administration Vz/F: Apparent volume of distribution at terminal phase

II. Description of the Embodiments

In one embodiment, the present invention provides an oral dosage form comprising a therapeutically effective amount of Compound A or pharmaceutically acceptable salts thereof and at least one pharmaceutically acceptable excipient, wherein said therapeutically effective amount is single daily dose to achieve a mean Cmax of from about 1.8 ng/mL to about 7.6 ng/mL for each 1 mg of Compound A after administration to human subjects.

In one embodiment, the present invention provides an oral dosage form comprising a therapeutically effective amount of Compound A or pharmaceutically acceptable salts thereof and at least one pharmaceutically acceptable excipient, wherein said therapeutically effective amount is single daily dose to achieve a mean Cmax of from about 1.8 ng/mL to about 7.6 ng/mL for each 1 mg of Compound A after administration to human subjects, and wherein said single daily dose ranges from about 25 mg to about 400 mg.

In one embodiment, the present invention provides an oral dosage form comprising a therapeutically effective amount of Compound A or pharmaceutically acceptable salts thereof and at least one pharmaceutically acceptable excipient, wherein said therapeutically effective amount is single daily dose to achieve a mean Cmax of from about 1.8 ng/mL to about 7.6 ng/mL for each 1 mg of Compound A after administration to human subjects, and wherein said therapeutically effective amount is single daily dose to achieve a mean AUC(0-inf) of from about 72.6 to about 217.0 ng*hr/mL for each 1 mg of Compound A after administration to human subjects.

In one embodiment, the present invention provides an oral dosage form comprising a therapeutically effective amount of Compound A or pharmaceutically acceptable salts thereof and at least one pharmaceutically acceptable excipient, wherein said therapeutically effective amount is single daily dose to achieve a mean Cmax of from about 1.8 ng/mL to about 7.6 ng/mL for each 1 mg of Compound A after administration to human subjects, and wherein said therapeutically effective amount is single daily dose to achieve a mean AUC(0-t) of from about 71.0 to about 210.0 ng*hr/mL for each 1 mg of Compound A after administration to human subjects.

In further embodiment, the present invention provides an oral dosage form for treating Alzheimer's disease or Lewy body dementia comprising a therapeutically effective amount of Compound A or pharmaceutically acceptable salts thereof and at least one pharmaceutically acceptable excipient, wherein said therapeutically effective amount is single daily dose to achieve a mean Cmax of from about 1.8 ng/mL to about 7.6 ng/mL for each 1 mg of Compound A after administration to human subjects.

In further embodiment, the present invention provides an oral dosage form for treating Alzheimer's disease or Lewy body dementia comprising a therapeutically effective amount of Compound A or pharmaceutically acceptable salts thereof and at least one pharmaceutically acceptable excipient, wherein said therapeutically effective amount is single daily dose to achieve a mean Cmax of from about 1.8 ng/mL to about 7.6 ng/mL for each 1 mg of Compound A after administration to human subjects, and wherein said single daily dose ranges from about 25 mg to about 400 mg.

In further embodiment, the present invention provides an oral dosage form for treating Alzheimer's disease or Lewy body dementia comprising a therapeutically effective amount of Compound A or pharmaceutically acceptable salts thereof and at least one pharmaceutically acceptable excipient, wherein said therapeutically effective amount is single daily dose to achieve a mean Cmax of from about 1.8 ng/mL to about 7.6 ng/mL for each 1 mg of Compound A after administration to human subjects, and wherein said therapeutically effective amount is single daily dose to achieve a mean AUC(0-inf) of from about 72.6 to about 217.0 ng*hr/mL for each 1 mg of Compound A after administration to human subjects.

In further embodiment, the present invention provides an oral dosage form for treating Alzheimer's disease or Lewy body dementia comprising a therapeutically effective amount of Compound A or pharmaceutically acceptable salts thereof and at least one pharmaceutically acceptable excipient, wherein said therapeutically effective amount is single daily dose to achieve a mean Cmax of from about 1.8 ng/mL to about 7.6 ng/mL for each 1 mg of Compound A after administration to human subjects, and wherein said therapeutically effective amount is single daily dose to achieve a mean AUC(0-t) of from about 71.0 to about 210.0 ng*hr/mL for each 1 mg of Compound A after administration to human subjects.

In another embodiment, the present invention provides an oral dosage form comprising about 25 mg to about 400 mg of Compound A or pharmaceutically acceptable salts thereof and at least one pharmaceutically acceptable excipient.

In another embodiment, the present invention provides an oral dosage form comprising about 25 mg to about 400 mg of Compound A or pharmaceutically acceptable salts thereof and at least one pharmaceutically acceptable excipient, wherein said Compound A or pharmaceutically acceptable salts thereof at a single daily dose achieves a mean Cmax of from about 1.8 ng/mL to about 7.6 ng/mL for each 1 mg of Compound A after administration to human subjects.

In another embodiment, the present invention provides an oral dosage form comprising about 25 mg to about 400 mg of Compound A or pharmaceutically acceptable salts thereof and at least one pharmaceutically acceptable excipient, wherein said Compound A or pharmaceutically acceptable salts thereof at a single daily dose achieves a mean AUC (0-inf) of from about 72.6 to about 217.0 ng*hr/mL for each 1 mg of Compound A after administration to human subjects.

In another embodiment, the present invention provides an oral dosage form comprising about 25 mg to about 400 mg of Compound A or pharmaceutically acceptable salts thereof and at least one pharmaceutically acceptable excipient, wherein said Compound A or pharmaceutically acceptable salts thereof at a single daily dose achieves a mean AUC(0-t) of from about 71.0 to about 210.0 ng*hr/mL for each 1 mg of Compound A after administration to human subjects.

In further embodiment, the present invention provides an oral dosage form for treating Alzheimer's disease or Lewy body dementia comprising about 25 mg to about 400 mg of Compound A or pharmaceutically acceptable salts thereof and at least one pharmaceutically acceptable excipient.

In further embodiment, the present invention provides an oral dosage form for treating Alzheimer's disease or Lewy body dementia comprising about 25 mg to about 400 mg of Compound A or pharmaceutically acceptable salts thereof and at least one pharmaceutically acceptable excipient, wherein said Compound A or pharmaceutically acceptable salts thereof at a single daily dose achieves a mean Cmax of from about 1.8 ng/mL to about 7.6 ng/mL for each 1 mg of Compound A after administration to human subjects.

In further embodiment, the present invention provides an oral dosage form for treating Alzheimer's disease or Lewy body dementia comprising about 25 mg to about 400 mg of Compound A or pharmaceutically acceptable salts thereof and at least one pharmaceutically acceptable excipient, wherein said Compound A or pharmaceutically acceptable salts thereof at a single daily dose achieves a mean AUC(0-inf) of from about 72.6 to about 217.0 ng*hr/mL for each 1 mg of Compound A after administration to human subjects.

In further embodiment, the present invention provides an oral dosage form for treating Alzheimer's disease or Lewy body dementia comprising about 25 mg to about 400 mg of Compound A or pharmaceutically acceptable salts thereof and at least one pharmaceutically acceptable excipient, wherein said Compound A or pharmaceutically acceptable salts thereof at a single daily dose achieves a mean AUC(0-t) of from about 71.0 to about 210.0 ng*hr/mL for each 1 mg of Compound A after administration to human subjects.

In yet another embodiment, the present invention provides a method of treating Alzheimer's disease or Lewy body dementia, comprising administering orally to a human subject in need thereof a dosage form with a therapeutically effective amount of Compound A or pharmaceutically acceptable salts thereof, wherein said therapeutically effective amount is single daily dose to achieve a mean Cmax of from about 1.8 ng/mL to about 7.6 ng/mL for each 1 mg of Compound A after administration to the human subject.

In yet another embodiment, the present invention provides a method of treating Alzheimer's disease or Lewy body dementia, comprising administering orally to a human subject in need thereof a dosage form with a therapeutically effective amount of Compound A or pharmaceutically acceptable salts thereof, and wherein said single daily dose ranges from about 25 mg to about 400 mg.

In yet another embodiment, the present invention provides a method of treating Alzheimer's disease or Lewy body dementia, comprising administering orally to a human subject in need thereof a dosage form with a therapeutically effective amount of Compound A or pharmaceutically acceptable salts thereof, wherein said therapeutically effective amount is single daily dose to achieve a mean Cmax of from about 1.8 ng/mL to about 7.6 ng/mL for each 1 mg of Compound A after administration to the human subject, and wherein said therapeutically effective amount is single daily dose to achieve a mean AUC(0-inf) of from about 72.6 to about 217.0 ng*hr/mL for each 1 mg of Compound A after administration to the human subject.

In yet another embodiment, the present invention provides a method of treating Alzheimer's disease or Lewy body dementia, comprising administering orally to a human subject in need thereof a dosage form with a therapeutically effective amount of Compound A or pharmaceutically acceptable salts thereof, wherein said therapeutically effective amount is single daily dose to achieve a mean Cmax of from about 1.8 ng/mL to about 7.6 ng/mL for each 1 mg of Compound A after administration to the human subject, and wherein said therapeutically effective amount is single daily dose to achieve a mean AUC(0-t) of from about 71.0 to about 210.0 ng*hr/mL for each 1 mg of Compound A after administration to the human subject.

In the present invention, preferred single daily dose of Compound A or pharmaceutically acceptable salts thereof ranges from about 25 mg to about 200 mg, from about 50 mg to about 200 mg, from about 75 mg to about 400 mg, from about 75 mg to about 200 mg, from about 100 mg to about 400 mg or from about 100 mg to about 200 mg.

In the present invention, preferred therapeutically effective amount is single daily dose to achieve a mean Cmax of from about 2.2 ng/mL to about 4.7 ng/mL for each 1 mg of Compound A after administration to the human subject.

In the present invention, preferred therapeutically effective amount is single daily dose to achieve a mean AUC(0-inf) of from about 89.6 to about 187.5 ng*hr/mL for each 1 mg of Compound A after administration to the human subject.

In the present invention, preferred therapeutically effective amount is single daily dose to achieve a mean AUC(0-t) of from about 88.0 to about 185.0 ng*hr/mL for each 1 mg of Compound A after administration to the human subject.

In the present invention, Compound A may be in the form of free form, a pharmaceutically acceptable salt, hydrate, solvate, polymorph or any combination of the foregoing.

Pharmaceutically acceptable salts may include, but are not limited to, inorganic acid salts; organic carboxylates; organic sulfonates; amino acid salts; quaternary amine salts; alkaline metal salts; and alkaline-earth metal salts. Preferred pharmaceutically acceptable salts include a maleate.

Oral dosage forms of the present invention include capsules, granules, lozenges, pellets, pills, powders, suspensions, tablets, preferably capsules, granules, pellets, pills, tablets.

The oral dosage form of the present invention may be prepared, using standard techniques and manufacturing processes generally known in the art. See, e.g. the monograph of Japanese Pharmacopoeia 16 edition or General Chapter <1151> Pharmaceutical Dosage Forms of U.S. Pharmacopoeia-NF (37).

EXAMPLES

The following examples illustrate various aspects of the present invention. They are not to be construed to limit the claims in any manner whatsoever.

Compound A monomaleate salt was synthesized according to the method described in WO2014/163147.

In Vivo Test (Effects of Compound A monomaleate salt on Scopolamine-Induced Memory Impairment in Rat Novel Object Recognition Test)

The effects of orally administered Compound A monomaleate salt on scopolamine-induced memory impairment in a novel object recognition test in rats was examined.

A scopolamine model is available as an animal model of Alzheimer's disease, Lewy body type dementia and, parkinson's disease with dementia. In Alzheimer's disease, Lewy body dementia, and parkinson's disease with dementia, the dysfunction of acetylcholine nervous system was observed (Whitehouse et al., "Alzheimer's disease and senile dementia: loss of neurons in the basal forebrain.", Science, vol. 215 (1982), pp. 1237-9; Shimada et al., "Mapping of brain acetylcholinesterase alterations in Lewy body disease by PET", Neurology, vol. 73 (2009), pp. 273-8; Tiraboschi et al., "Cholinergic dysfunction in diseases with Lewy bodies", Neurology, vol. 54, (2000) pp. 407-411; Perry et. al., "Neocortical cholinergic activaties differentiate Lewy body dementia from classical Alzheimer's disesase", NeuroReport, vol. 5 (1994), pp. 747-9). Scopolamine is a muscarinic receptor antagonist and blocks the transmission of acetylcholine nervous system. The acetylcholine nervous system is involved in memory and attention etc. Healthy subjects and animals administered scopolamine showed dementia-like amnesia, and scopolamine-induced amnestic symptoms improved with compounds used to treat cognitive impairment of Alzheimer's disease and Lewy body disease (Snyder et al., "Reversal of scopolamine-induced deficits with a single dose of donepezil, an acetylcholinesterase inhibitor", Alzheimer's & Dementia 1 (2005) pp. 126-135; Sambeth et al., "Cholinergic drugs affect novel object recognition in rats: Relation with hippocampal EEG?", European Journal of Pharmacology, vol. 572 (2007) pp. 151-159). A novel object recognition test is based on the greater spontaneous exploration of a novel object, compared with a familiar object, observed in rodents (Ennaceur and Delacour, "A new one-trial test for neurobiological studies of memory in rats. 1: Behavioral data", Behavioural Brain Research, 31 (1988) pp. 47-59). The test is considered a model of recognition memory and does not involve appetitive or aversive reinforcement. Therefore, it is considered to be analogous to recognition memory tests used in human clinical testing.

Materials and Methods

Six-week-old male Long-Evans rats (Institute for Animal Reproduction) were used in this study. Before test day, rats were placed in each experimental apparatus once a day, on two consecutive days to habituate rats to the test chamber. Each habituation session, consisted of a 3 minutes exposure to the empty test arena (40 cm×30 cm×45 cm tall), followed by approximately 1 minute in the side annex (13 cm×30 cm×45 cm tall), and a further 5 minutes in the test arena. Animals were dosed with oral vehicle and intraperitoneal saline before first 3 minutes exposure on each day.

On the test day, Compound A monomaleate salt or vehicle (0.01 mol/L-HCl in 0.5% methyl cellulose, 10 mL/kg) was orally administered to the rats after randomization (n=8 per group). After 1.5 hours, scopolamine (0.7 mg/kg, Wako Pure Chemical Industries) or saline (1 mL/kg) was intraperitoneally administered. An acquisition trial (T1) was conducted 30 minutes after the administration of scopolamine. In the T1, after the rats were habituated to the empty test arena for 3 minutes, the rats were placed into the side annex, and two identical objects were placed into the test arena. The rats were then returned to each arena and allowed to freely explore the two identical objects for 5 minutes. After this exploration, they were returned to their home cage once.

Following a 2-hour intertrial interval, a retention trial (T2) was conducted. After 3 minutes habituation to the empty test arena, the rats were placed into the side annex and one object used in the T1 trial ("familiar" object) and one object unused in the T1 trial ("novel" object) were placed into the test arena. The rats were again returned to each test arena in which these objects were placed, and allowed to freely explore the objects for 3 minutes. All objects were cleaned with wet wipes contained water and ethanol between trials to remove olfactory traces. Animal performance in T1 and T2 was recorded with a digital video camera, and the amount of time spent exploring each object was measured by manual stopwatches. Exploration was defined as the behavior which the rat was bringing its nose within 2 cm close to the object and the nose was directed at the object. The experiment was repeated twice.

In novel object recognition test, the following novel object exploration ratio in T2 is considered as amnesic indexes reflecting the discrimination between the familiar and novel objects. These indexes are calculated according to the following formulas:

$$\text{Novel object exploration ratio}(\%) = \frac{N}{(N+F)} \times 100 \qquad \text{[Math. 1]}$$

F: familiar object exploration time (s)
N: novel object exploration time (s)

The following rats were excluded from data analyses; rats with exploration of objects totaling less than 10 seconds in T1 or T2, or exploration of one of the two identical objects more than 70% or less than 30% in T1.

Data are expressed as the mean±SEM. The difference between the non-scopolamine treated control and scopolamine treated control groups were analyzed using unpaired t test. The effects of Compound A monomaleate salt on novel object exploration ratio in T2 was analyzed by one-way analysis of variance (ANOVA) followed by the Dunnett multiple comparison test. A value of P<0.05 (two sided) was considered statistically significant. Statistical analyses were performed using the GraphPad Prism version 5.04 (GraphPad Software). The results are shown in Table 1.

cGMP in the cerebrospinal fluid (hereinafter referred to as "CSF cGMP") elevation in each sample was measured according to the method described in WO2013/051639. The results are shown in Table 2.

Results

In T2, the vehicle and saline treated rats spent relatively more time exploring the novel object. In rat novel object recognition test, a relative increase in the amount of time spent exploring the novel object compared with the familiar object was considered to reflect retention of the memory for the familiar object.

The rats treated with scopolamine showed significantly lowering novel object exploration ratio than those which saline treated rats did. These findings indicated the scopolamine-induced memory impairment in rats.

A significant memory-improving effect of orally administered Compound A monomaleate salt on scopolamine-induced memory impairment was observed at both 3.3 and 10 mg/kg in rats. This result suggests that Compound A monomaleate salt is expected to enhance cognitive function.

TABLE 1

|  | Saline/Vehicle | Scopolamine/Vehicle | Scopolamine/Compound A (3.3 mg/kg) | Scopolamine/Compound A (10 mg/kg) |
| --- | --- | --- | --- | --- |
| Novel object exploration ratio (%) | 73.8 ± 3.0 | 53.3 ± 2.2* | 68.5 ± 2.0[#] | 68.5 ± 1.6[#] |

In Table 1, data represent the mean±SEM values (N=15 or 16) for the novel object exploration ratio in T2 (time spent exploring novel object in T2 divided by total object exploration in T2). Non-scopolamine treated control groups (Saline/Vehicle) and scopolamine treated control groups (Scopolamine/Vehicle) were used for comparison in each study. *$P<0.05$: versus Saline/Vehicle (unpaired t test). # $P<0.05$: versus Scopolamine/Vehicle (one-way ANOVA followed by the Dunnett multiple comparison test).

TABLE 2

|  | Saline/Vehicle | Scopolamine/Vehicle | Scopolamine/Compound A (3.3 mg/kg) | Scopolamine/Compound A (10 mg/kg) |
| --- | --- | --- | --- | --- |
| CSF cGMP conc. (nM) (% CSF cGMP increase from vehicle control) | 1.94 ± 0.297 (—) | 2.012 ± 0.154 (4) | 3.694 ± 0.65 (90) | 4.889 ± 0.538 (152) |

According to the test results, it is considered that about 200% CSF cGMP elevation has improved a cognitive effect. Therefore, about 200% CSF cGMP elevation in human subjects was expected to achieve a therapeutic effect in a human subject Clinical Trial Preparation of Capsules Containing Compound a Monomaleate Salt 387 g of Compound A monomaleate salt, 378 g of anhydrous lactose (DFE Pharma Corp.), 150 g of low-substituted hydroxypropyl cellulose (Type LH21, Shinetsu Chemical Co., Ltd.), 50.0 g of hydroxypropyl cellulose (Type L, Nippon Soda Co., Ltd.) and 30.0 g of crospovidone (XL-10, DSP Gokyo Food & Chemical Co., Ltd.) were mixed in a high shear mixer. 5.0 g of Magnesium stearate was added into the mixer and then mixed. The resulting physical mixture was compacted into the ribbon by using a roller compactor. The ribbon was sized using a screen mill equipped with sieve having 1 mm openings. 16.666 mg or 166.66 mg of the resulting granules was filled into capsule shells using an encapsulation machine.

In the following examples and tables, a dose of Compound A is described as a value in terms of Compound A free form.

Objectives

Primary Objectives

1. To evaluate the safety, tolerability, and pharmacokinetics (PK) of single ascending oral doses of Compound A in healthy adult subjects
2. To evaluate the safety, tolerability, and PK of a single oral dose of Compound A in healthy elderly subjects
3. To evaluate the pharmacodynamic (PD) effects of single oral doses of Compound A on cyclic guanosine monophosphate (cGMP) in cerebrospinal fluid (CSF), and the PK/PD relationship in healthy adult subjects
4. To evaluate the safety, tolerability, and PK of Compound A in Japanese subjects following administration of single oral doses at 3 dose levels Secondary Objectives 1. To evaluate the effects of a high fat meal on the PK of a single oral dose of Compound A in healthy adult subjects
2. To compare the PK of Compound A between Japanese subjects and non-Japanese subjects Methodology This was a single center, single dose, randomized, double blind, placebo controlled study in healthy subjects. It consisted of 4 parts: Parts A, B, C, and D. Each of the four study parts had 2 phases: Prerandomization Phase and Randomization Phase. The Prerandomization Phase lasted up to 30 days and consisted of a Screening Period and a Baseline Period, during which each subject's study eligibility was determined and baseline assessments were performed.

For subjects who did not participate in the evaluation of food effect (Parts A, C, and D), the Randomization Phase consisted of the Treatment Period and a Follow Up Period. During the Treatment Period, subjects were randomized to receive a single oral dose of either Compound A or matching placebo. Subjects were admitted to the clinic on Day 2 for baseline assessments and discharged on Day 5. They returned to the clinic as outpatients on Days 6 and 7 for study assessments. A Follow Up Visit took place on Day 10. For subjects who participated in the evaluation of food effect (Part B), the Randomization Phase consisted of Treatment Period 1, Baseline Period 2, and Treatment Period 2. During Treatment Period 1, subjects were randomly assigned to receive a single oral dose of either Compound A or matching placebo after an overnight fast. Subjects were admitted to clinic on Day 2 (Baseline Period 1) for baseline assessments and discharged on Day 5 (Treatment Period 1). They returned to the clinic as outpatients on Days 6, 7, and 10 (Treatment Period 1) for study assessments. After a washout period of at least 13 days (or 5 half lives of Compound A, whichever was longer), they were admitted again to clinic for baseline assessments during Baseline Period 2 (Day 1 of Period 2). During Day 1 of Treatment Period 2, following an overnight fast of at least 10 hours, subjects started to consume a high-fat (approximately 50% of total caloric content of the meal) and high-calorie (approximately 800 to 1000 calories) meal 30 minutes before administration of study drug. The subjects were administered study drug with 240 mL of water 30 minutes after the start of the meal, regardless of how much of the meal had been consumed at that point. Water was allowed as desired except for 1 hour before and after dosing. Subjects were discharged on Day 5 of Treatment Period 2 and returned to the clinic as outpatients on Days 6 (Treatment Period 2) and 7 (Treatment Period 2) for study assessments. A Follow Up Visit occurred on Day 10 (Treatment Period 2). The end of the study was the date of the last study visit for the last subject.

Part A

In Part A, there were 8 sequential cohorts of healthy adult subjects (18-50 years of age). Subjects were randomly assigned to Compound A or placebo in a ratio of 6:2, respectively. Subjects in the Compound A cohorts were treated with single ascending doses of 10, 25, 50, 100, 200, 400, 800, or 1200 mg.

After the Screening Period, subjects returned to the clinic on Day 2 for Baseline procedures. Subjects were treated with study drug on Day 1 in the morning after an overnight fast. Blood and urine PK samples were collected at prespecified time points. Safety evaluations were also performed.

Dose escalation for Part A occurred only after formal communication with the sponsor. Before deciding whether to escalate to the next dose, data for the whole cohort of subjects were required. Escalation to the next higher dose level only occurred if the available data supported the increase to the next dose. Data from each completed cohort remained blinded during review by the sponsor in determining progression of doses for each cohort. Subjects in Part A did not participate in the evaluation of PD or food effect and had 1 Treatment Period, with their Follow Up Visit on Day 10.

Part B

In Part B, there were 4 cohorts of healthy adult subjects (18-50 years of age). There were 8 subjects in Cohort 1, with 6 subjects randomly assigned to receive single doses of Compound A (400 mg) and 2 subjects randomly assigned to receive placebo. There were 7 subjects in Cohort 2 and Cohort 3, each with 6 subjects randomly assigned to receive single doses of Compound A (100 and 200 mg, respectively) and 1 subject randomly assigned to receive placebo. The dose of 100 mg selected in Cohort 2 was based on preliminary analysis of Cohort 1 data; this dose was predicted from PK/PD modeling to achieve a sustained CSF cGMP increase from baseline of approximately 200% when administered to steady state, and thereby provided a potentially therapeutic dose for further evaluation in future studies. There were 7 subjects in Cohort 4, with 6 subjects randomly assigned to receive a single dose of Compound A (50 mg [n=3] or 75 mg [n=3]) and 1 subject randomly assigned to receive placebo. The doses for Cohorts 3 and 4 were selected based on PK/PD modeling of the data in Cohorts 1 and 2.

After the Screening Period, subjects returned to the clinic on Day 2 for Baseline procedures. Subjects had a lumbar catheter inserted on Day 1. Serial CSF sampling via the lumbar catheter commenced on Day 1, after an overnight fast. CSF samples were collected on Day 1 over a period of 3 hours predose. Subjects were then administered study drug, and serial CSF sampling for 30 hours postdose was performed to determine CSF cGMP and CSF Compound A concentrations. Blood samples for plasma Compound A PK were collected at the same time points as CSF sampling. Safety evaluations were also performed.

Subjects in Cohort 2 who had received Compound A 100 mg or placebo under fasted conditions (1st Treatment Period) also participated in an evaluation of food effect on the PK of Compound A (2nd Treatment Period). After a washout period of at least 13 days (or 5 half-lives of Compound A, whichever was longer), subjects were admitted to the clinic for baseline assessments (2nd Baseline Period) and then received a single dose of the same treatment (Compound A 100 mg or placebo) after consuming a high fat and high calorie meal over 30 minutes. Blood PK samples were collected at prespecified time points. Safety evaluations were also assessed. CSF was not collected for PD evaluation during the 2nd Treatment Period. A Follow Up Visit occurred on Day 10 of Treatment Period 2.

Part C

In Part C, there was 1 cohort of 8 healthy elderly subjects (65 to 85 years of age) randomly assigned to receive a single dose of Compound A 100 mg or placebo in a ratio of 6:2, respectively.

After the Screening Period, subjects returned to the clinic on Day 2 for Baseline procedures. Subjects were administered study drug on Day 1 in the morning after an overnight fast. The blood and urine PK samples were collected at prespecified time points. Safety evaluations were also performed. Subjects in Part C did not participate in the evaluation of PD or food effect and had 1 Treatment Period, with their Follow Up Visit on Day 10.

Part D

In Part D, 3 cohorts of healthy adult Japanese subjects were randomized in parallel. There were 7 subjects in each cohort and subjects were randomly assigned to receive single doses of Compound A (25, 100, or 400 mg) or placebo in a ratio of 6:1, respectively.

Subjects in each cohort were matched by age (plus or minus 10 years) to subjects in the corresponding dose cohort in Part A. The distribution of gender in each Japanese cohort was also matched approximately to the corresponding dose cohort in Part A.

After the Screening Period, subjects returned to the clinic on Day −2 for Baseline procedures. They were administered study drug on Day 1 in the morning after an overnight fast. Blood PK samples were collected at prespecified time points. Safety evaluations were also performed. Subjects in Part D did not participate in the evaluation of PD or food effect and had 1 Treatment Period, with their Follow Up Visit on Day 10.

Number of Subjects (Planned and Enrolled)

Part A: Up to 64 healthy adult subjects were planned; 64 subjects were enrolled

Part B: Up to 29 healthy adult subjects were planned; 29 subjects were enrolled

Part C: 8 healthy elderly subjects were planned and enrolled

Part D: 21 healthy Japanese adult subjects were planned and enrolled

Diagnosis and Main Criteria for Inclusion

Parts A and B Only

1. Nonsmoking, male or female subjects greater than or equal to 18 years of age and less than or equal to 50 years of age at the time of informed consent Part C Only 1. Nonsmoking, male or female subjects greater than or equal to 65 years of age and less than or equal to 85 years of age at the time of informed consent Parts A, B, C, and D 1. Body mass index (BMI) greater than or equal to 18 and less than or equal to 30 kg/m$^2$ at Screening Part D Only 1. Nonsmoking, male or female subjects greater than or equal to 20 years of age and less than or equal to 50 years of age at the time of informed consent 2. Born in Japan to Japanese parents with grandparents of Japanese descent 3. Had been living outside Japan for less than 5 years 4. Lifestyle, including diet, had not changed significantly since leaving Japan Diagnosis and Main Criteria for Exclusion 1. Clinically significant illness that required medical treatment within 8 weeks or a clinically significant infection that required medical treatment within 4 weeks of dosing 2. Evidence of disease that could have influenced the outcome of the study within 4 weeks before dosing; eg, psychiatric disorders and disorders of the gastrointestinal tract, liver, kidney, respiratory system, endocrine system, hematological system, neurological system, or cardiovascular system, or subjects who had a congenital abnormality in metabolism 3. Any history of abdominal surgery that could have affected PK profiles of Compound A (eg, hepatectomy, nephrectomy, digestive organ resection) at Screening or Baseline
4. A prolonged QT/QTc interval (QTc greater than 450 ms) demonstrated on ECG at Screening or Baseline; a history of risk factors for torsade de pointes (eg, heart failure, hypokalemia, or family history of long QT Syndrome) or the use of concomitant medications that prolonged the QT/QTc interval
5. Left bundle branch block
6. History of myocardial infarction or active ischemic heart disease
7. History of clinically significant arrhythmia or uncontrolled arrhythmia
8. Persistent systolic blood pressure (BP) greater than 130 mmHg or diastolic BP greater than 85 mmHg at Screening or Baseline (Parts A, B, and D)
9. Persistent systolic BP greater than 140 mmHg or diastolic BP greater than 90 mmHg at Screening or Baseline (Part C)
10. Heart rate less than 50 or more than 100 beats/min at Screening or Baseline
11. Known history of clinically significant drug allergy at Screening or Baseline
12. Known history of food allergies or was experiencing significant seasonal or perennial allergy at Screening or Baseline
13. Intake of caffeinated beverages or food within 72 hours before dosing
14. Intake of nutritional supplements, juice, and herbal preparations or other foods or beverages that may have affected the various drug metabolizing enzymes and transporters (eg, alcohol, grapefruit, grapefruit juice, grapefruit containing beverages, apple or orange juice, vegetables from the mustard green family [eg, kale, broccoli, watercress, collard greens, kohlrabi, brussel sprouts, or mustard], and charbroiled meats) within 1 week before dosing
15. Intake of herbal preparations containing St. John's Wort within 4 weeks before dosing
16. Use of prescription drugs within 4 weeks before dosing
17. Intake of over the counter (OTC) medications within 2 weeks before dosing
18. Engagement in strenuous exercise within 2 weeks before check in (eg, marathon runners, weight lifters)
19. Any contraindication to continuous CSF sampling via indwelling lumbar catheter (Part B only)

Test Treatment, Dose, Mode of Administration, and Batch Number(s)

Test Treatment: Compound A was administered orally at 10, 25, 50, 100, 200, 400, 800, and 1200 mg in size No. 2, hydroxypropyl methylcellulose (HPMC) capsules containing 5 mg or 50 mg of Compound A.

Reference Therapy, Dose, Mode of Administration, and Batch Number(s)

Comparator Drug: Matching placebo capsules (Manufactured Lot: P49001ZZ, Labeled Lot: P4A05) were administered orally in size No. 2, HPMC capsules containing mannitol.

Duration of Treatment
Parts A, C, and D: Single dose on Day 1
Part B (all Cohorts): Single dose on Day 1
Part B (100 mg Cohort): Single dose on Day 1 of Treatment Period 1 and on Day 1 of Treatment Period 2

Pharmacokinetics
Pharmacokinetic Assessments for Parts A, C, and D—Plasma

Blood samples for determination of plasma Compound A concentrations were collected from predose to 216 hours postdose. On Day 1, blood PK samples were collected at predose and postdose 0.5 (30 minutes), 1, 1.5, 2, 3, 4, 5, 6, 8, 12, and 18 hours. Thereafter, samples were collected on Day 2 (24 and 36 hours postdose), Day 3 (48 hours postdose), Day 4 (72 hours postdose), Day 5 (96 hours postdose), Day 6 (120 hours postdose), Day 7 (144 hours postdose), and Day 10 (216 hours postdose).

Pharmacokinetic Assessments for Part B—Plasma

Blood samples for determination of plasma Compound A concentrations were collected from predose to 216 hours postdose. For all cohorts, blood PK samples were collected on Day 1 at predose and postdose at 0.5 (30 minutes), 1, 1.5, 2, 3, 4, 5, 6, 8, 10, 12, and 18 hours. Thereafter, samples were collected on Day 2 (24, 30, and 36 hours postdose), Day 3 (48 hours postdose), Day 4 (72 hours postdose), Day 5 (96 hours postdose), Day 6 (120 hours postdose), Day 7 (144 hours postdose), and Day 10 (216 hours postdose). For subjects in Cohort 2 of Part B only, in addition to Day 1 to Day 10 of Treatment Period 1, blood PK samples were also collected on the following days of Treatment Period 2: Day 1 at predose and postdose 0.5 (30 minutes), 1, 1.5, 2, 3, 4, 5, 6, 8, 10, 12, and 18 hours. Thereafter, samples were collected on Day 2 (24, 30, and 36 hours postdose), Day 3 (48 hours postdose), Day 4 (72 hours postdose), Day 5 (96 hours postdose), Day 6 (120 hours postdose), Day 7 (144 hours postdose), and Day 10 (216 hours postdose).

Pharmacokinetic Assessments for Part B—Cerebrospinal Fluid

Concentrations of Compound A in CSF were analyzed in serial CSF samples collected at predose and postdose at 1, 2, 3, 4, 5, 6, 8, 10, 12, 14, 16, 18, 24, and 30 hours.

Pharmacokinetic Assessments for Part A and C—Urine

Urine Compound A concentrations were analyzed predose and up to 96 hours postdose.

Pharmacodynamic Assessments for Part B—Cerebrospinal Fluid

Serial CSF samples were collected from the lumbar catheter for analysis of concentrations of cyclic guanidine monophosphate (cGMP) at −3, −2, −1 hours, predose (0 hour), and postdose at 1, 2, 3, 4, 5, 6, 8, 10, 12, 14, 16, 18, 24, and 30 hours.

Safety Assessments

Safety assessments consisted of monitoring and recording all adverse events (AEs) and serious adverse events (SAEs); laboratory evaluation for hematology, blood chemistry, and urine values; periodic measurement of vital signs (including orthostatic changes in blood pressure [BP] and heart rate [HR]) and electrocardiograms (ECGs); and the performance of physical examinations.

In addition, high precision QTcF analysis using Holter ECG recording was conducted in Parts A, C, and D during Day −1 and Day 1, to allow more rigorous assessments of possible changes in QTcF intervals. A central ECG laboratory was used to extract ECG recordings from the Holter device.

Bioanalytical Methods

Plasma, urine and CSF concentrations of Compound A were measured using validated liquid chromatography mass spectrometry/mass spectrometry (LC MS/MS) assay methods. CSF concentrations of cGMP were measured using a validated LC-MS/MS assay method.

Statistical Methods
Analysis Sets

The Safety Analysis Set was the group of subjects who received at least 1 dose of study drug and had at least 1 postdose safety assessment.

The PK Analysis Set was the group of subjects who had sufficient PK data to derive at least 1 PK parameter.

The PD Analysis Set was the group of subjects who had sufficient PD data to derive at least 1 PD parameter.

The total number of enrolled subjects was tabulated. In addition, the number and percentage of subjects was tabulated by treatment group for the Safety Analysis Set, PK Analysis Set and PD Analysis Set.

Pharmacokinetic Analyses—Plasma

The following PK parameters were derived by noncompartmental analysis using plasma Compound A concentrations:

Cmax: maximum observed concentration
tmax: time at which the highest drug concentration occurs
AUC(0-24 h): area under the concentration-time curve from zero time to 24 hours postdose
AUC(0-30 h): area under the concentration-time curve from zero time to 30 hours postdose (Part B only)
AUC(0-72 h): area under the concentration-time curve from zero time to 72 hours postdose
AUC(0-t): area under the concentration-time curve from zero time to time of last quantifiable concentration
AUC(0-inf): area under the concentration-time curve from zero time extrapolated to infinite time
t1/2: terminal elimination phase half-life
CL/F: apparent total clearance following extravascular (eg, oral) administration
Vz/F: apparent volume of distribution at terminal phase Pharmacokinetic Analyses—CSF (Part B only)

The following PK parameters were derived by noncompartmental analysis using CSF Compound A concentrations:

Cmax: maximum drug concentration
tmax: time to reach maximum (peak) concentration following drug administration
AUC(0-24 h): area under the concentration-time curve from zero time to 24 hours postdose
AUC(0-30 h): area under the concentration-time curve from zero time to 30 hours postdose
AUC(0-t): area under the concentration-time curve from zero time to time of last quantifiable concentration
t1/2: terminal elimination half-life following last dose
CSF: plasma AUC ratio: ratio of AUC(0-t) for CSF to plasma (or AUC(0-30 h), which was the last time point for CSF collection)
CSF: plasma Cmax ratio: ratio of Cmax for CSF to plasma (reported as a percentage)

Pharmacokinetic Analyses—Urine (Parts A and C)

The following PK parameters were calculated for Compound A:

Ae (0-96 h): cumulative amount of drug excreted in urine up to 96 hours postdose
Fe(0-96 h): fraction of dose excreted in urine up to 96 hours postdose
CLR: renal clearance Pharmacodynamic Analyses (Part B Only)

The Safety Analysis Set was used for PD concentration listings. The PD Analysis Set was used for the summaries of PD concentrations and derivations and summaries of PD parameters.

The primary PD measure was CSF cGMP. The following PD parameters were reported for CSF cGMP:

Amax: Maximum change (%) of CSF cGMP concentration compared to baseline at a single time point within 30 hours postdose
TAmax: Time at which Amax occurs for CSF cGMP
AUAC(−3-0 h): Area under the CSF cGMP concentration× time curve from time −3 to 0 hours
AUAC(0-24 h): Area under the CSF cGMP concentration× time curve from time 0 to 24 hours
AUAC(0-30 h): Area under the CSF cGMP concentration× time curve from time 0 to 30 hours
ΔAUAC(0-24 h): Change (%) in AUAC averaged over 24 hours postdose relative to baseline AUAC averaged over 3 hours predose for CSF cGMP:
(AUAC(0-24 h)/24−AUAC(−3-0 h)/3)/(AUAC(−3-0 h)/3)
ΔAUAC(0-30 h): Change (%) in AUAC averaged over 30 hours postdose relative to baseline AUAC averaged over 3 hours predose for CSF cGMP:
(AUAC(0-30 h)/30−AUAC(−3-0 h)/3)/(AUAC(−3-0 h)/3)

Population Pharmacokinetics/Pharmacodynamics

Plasma Compound A concentrations pooled from all cohorts of the study were subjected to population PK analysis using nonlinear mixed effects modelling. The effect of covariates, such as baseline demographics/characteristics (eg, body weight, age, gender, ethnicity, etc) on the PK of Compound A were explored. The individual posterior estimates of PK parameters were then used to generate individual PK profiles of Compound A, which were used in subsequent PK/PD analysis of the percent change from baseline in CSF cGMP concentrations.

Safety Analyses

All safety analyses were performed on the Safety Analysis Set.

Safety data evaluated included AEs, clinical laboratory results, vital signs, and ECGs.

Treatment emergent adverse events (TEAEs) were summarized by presenting the incidence of AEs for each cohort and dose group. For the laboratory, vital signs, and ECG data in all cohorts in any treatment period, the baseline was the values recorded immediately prior to dosing with study drug in that treatment period.

Interim Analyses

No unblinded interim analyses were performed during this study and no formal interim analysis of safety, PK, and PD data was performed after completion of Parts A, B, or C. However, PK and PD analyses were conducted using blinded subject IDs with the completion of each cohort.

In addition, blinded analyses of PK and PD data from Cohorts 1 and 2 in Part B were conducted to assess the PK/PD relationship and to determine the optimal doses to be administered in Cohorts 3 and 4. Analyses of blinded data from Cohort 3 in Part B were also conducted to assess the PK/PD relationship to determine doses in Cohort 4.

Sample Size Rationale

In Parts A and C, 8 subjects per cohort (with 6 subjects randomized to Compound A and 2 subjects to placebo) were considered adequate to evaluate initial safety and PK in healthy subjects, and to support dose escalation decisions. In the Pfizer study of PF 04447943 (40 mg), CSF cGMP elevation was demonstrated in healthy subjects, and this study used a similar sample size (with 5 subjects on 40 mg of PF 04447943 and 2 on placebo). Thus, in Part B, 7 or 8 subjects per cohort (with 6 subjects randomized to Compound A in all Part B cohorts) was considered adequate to evaluate the PD effects of Compound A on CSF cGMP.

In Part D, 7 subjects (with 6 subjects randomized to Compound A and 1 subject to placebo) in each of the 3 cohorts were considered adequate to provide bridging safety and PK data in healthy Japanese subjects.

Results

Subject Disposition/Analysis Sets

Overall, 352 subjects were screened for entry into the study. Of these 352 subjects, 230 were screening failures and 122 were randomized into the study. Of the 230 screen failures, 151 (42.9%) subjects failed to meet inclusion or exclusion criteria, 1 (0.3%) subject experienced an adverse event (pretreatment), 19 (5.4%) subjects withdrew consent, and 59 (16.8%) subjects were excluded for other reasons.

In Part A, 64 (100%) healthy adult subjects were randomly assigned to Compound A or placebo treatment; 48 subjects received Compound A and 16 subjects received placebo. Forty-seven (97.9%) subjects in the Compound A groups and 16 subjects in the placebo group completed the study. One subject in the Compound A 800 mg group was withdrawn from the study due to "other" category; this subject was non-compliant and smelled of alcohol during the follow-up visit.

In Part B, 29 (100%) healthy adult subjects were randomly assigned to Compound A or placebo treatment; 24 subjects received Compound A and 5 subjects received placebo. All 29 subjects completed the study. Six subjects in the 100 mg cohort and 1 subject in the placebo cohort received two single doses of study drug under fasted and fed conditions.

In Part C, 8 (100%) healthy elderly subjects were randomly assigned to Compound A or placebo treatment; 6 subjects received Compound A 100 mg and 2 subjects received placebo. All 8 subjects completed the study. The 2 placebo subjects in the healthy elderly subject group are included with the 16 healthy younger adult subjects in the summary tables, making a total of 18 placebo subjects in the Parts A and C.

In Part D, a total of 21 (100%) healthy Japanese adult subjects were randomly assigned to Compound A or placebo treatment; 18 subjects received Compound A and 3 subjects received placebo. All 18 subjects in the Compound A groups completed the study. One (33.3%) subject in the placebo group withdrew from the study due to "other" category; this subject did not return for the Follow-Up Visit on Day 10.

Pharmacokinetics, Pharmacodynamics, Pharmacogenomics
Plasma Compound A Pharmacokinetics Data for healthy adult subjects in Parts A and B who were treated under fasted conditions at the same dose levels (ie, Compound A 50, 100, 200, or 400 mg) were pooled together for plasma Compound A summary statistics and PK analyses.

Healthy Adult Subjects:

The key plasma Compound A PK results for healthy adult subjects (Parts A and B combined) administered a single oral dose (10, 25, 50, 75, 100, 200, 400, 800, or 1200 mg) of study drug are summarized in Table 3. After single doses of 10 to 1200 mg, Compound A was rapidly absorbed with most subjects having quantifiable plasma Compound A concentrations within 0.5 hour postdose. Across all doses, the median tmax ranged from 2 to 4 hours postdose and Compound A showed biphasic disposition in the absorption profile after tmax. During the initial phase, plasma Compound A concentrations declined until approximately 12 hours postdose and then remained relatively stable through 24 hours postdose. At all dose levels, there were subjects who showed multiple secondary peaks during the first 24 hours postdose. At 24 hours postdose and onwards, Compound A showed first order kinetics during the terminal elimination phase. Mean t1/2 values ranged from 26.8 to 33.6 hours across all doses (10 to 1200 mg), with no trend of increasing t1/2 values with increasing doses. Overall the geometric mean (GM) Cmax values increased subproportionally with increasing doses from 10 to 1200 mg, but the GM Cmax of 800 mg was somewhat higher than expected from the general trend, which could be due to between cohort variability. Geometric mean AUC(0-inf) values increased subproportionally with each increasing dose from 10 to 1200 mg. Geometric mean CUF values increased with increasing doses.

TABLE 3

Summary of Plasma Compound A Pharmacokinetic Parameters in Healthy Adult Subjects in Parts A and B

| Parameter | Compound A | | | | | | | | |
|---|---|---|---|---|---|---|---|---|---|
| | 10 mg (N = 6) | 25 mg (N = 6) | 50 mg (N = 9) | 75 mg (N = 3) | 100 mg (N = 12) | 200 mg (N = 12) | 400 mg (N = 12) | 800 mg (N = 6) | 1200 mg (N = 6) |
| Cmax (ng/mL) GM (% CV) | 60.2 (47.5) | 152 (29.0) | 225 (21.2) | 222 (36.9) | 373 (19.8) | 539 (29.8) | 880 (27.3) | 2570 (21.8) | 1780 (18.7) |
| tmax (h) Median (Min, Max) | 2.27 (1.03, 4.05) | 2.65 (2.02, 4.08) | 4.00 (1.52, 5.00) | 3.00 (2.97, 7.98) | 2.99 (0.93, 8.03) | 2.00 (1.00, 12.10) | 2.50 (0.95, 18.02) | 3.55 (1.45, 4.20) | 3.02 (1.50, 24.00) |
| tlag (h) Median (Min, Max) | 0.50 (0.00, 0.53) | 0.00 (0.00, 0.00) | 0.00 (0.00, 0.52) | 0.00 (0.00, 0.50) | 0.00 (0.00, 0.50) | 0.00 (0.00, 0.50) | 0.00 (0.00, 0.48) | 0.00 (0.00, 0.00) | 0.00 (0.00, 0.00) |
| AUC(0-24 h) (h × ng/mL) GM (% CV) | 719 (24.7) | 1850 (17.9) | 3370 (23.8) | 3650 (25.3) | 5730 (13.2) | 7800 (25.2) | 12500 (18.5) | 29200 (12.5) | 28500 (18.2) |
| AUC(0-30 h) (h × ng/mL) GM (% CV) | 863 (21.8) | 2200 (16.4) | 4010 (23.6) | 4460 (23.1) | 6890 (13.3) | 9440 (24.7) | 15200 (18.0) | 34500 (13.3) | 34800 (19.6) |
| AUC(0-72 h) (h × ng/mL) GM (% CV) | 1430 (16.1) | 3570 (12.9) | 6490 (21.3) | 7880 (14.1) | 11900 (14.0) | 16800 (29.5) | 27000 (14.1) | 54700 (15.8) | 60600 (22.8) |
| AUC(0-t) (h × ng/mL) GM (% CV) | 1700 (16.8) | 4200 (16.6) | 7720 (24.8) | 9520 (6.52) | 14800 (19.6) | 22000 (41.8) | 35500 (21.3) | 64300 (19.9) | 78400 (32.2) |
| AUC(0-inf) (h × ng/mL) GM (% CV) | 1840 (15.5) | 4340 (18.5) | 7900 (25.3) | 9880 (4.64) | 15000 (20.0) | 22400 (42.5) | 36300 (22.9) | 65000 (20.2) | 79700 (33.2) |

TABLE 3-continued

Summary of Plasma Compound A Pharmacokinetic Parameters in Healthy Adult Subjects in Parts A and B

| Parameter | Compound A | | | | | | | | |
|---|---|---|---|---|---|---|---|---|---|
| | 10 mg (N = 6) | 25 mg (N = 6) | 50 mg (N = 9) | 75 mg (N = 3) | 100 mg (N = 12) | 200 mg (N = 12) | 400 mg (N = 12) | 800 mg (N = 6) | 1200 mg (N = 6) |
| $t_{1/2}$ (h) | 33.6 | 26.8 | 26.9 | 28.9 | 28.6 | 30.9 | 33.2 | 25.2 | 31.9 |
| Mean (SD) | (8.49) | (6.95) | (9.40) | (7.48) | (6.73) | (8.37) | (13.8) | (5.36) | (9.54) |
| CL/F (L/h) | 5.41 | 5.76 | 6.33 | 7.57 | 6.66 | 8.93 | 11.0 | 12.3 | 15.1 |
| GM (% CV) | (15.5) | (18.5) | (25.1) | (4.86) | (20.1) | (42.5) | (22.8) | (20.1) | (33.1) |
| Vz/F (L) | 255 | 216 | 233 | 308 | 268 | 384 | 493 | 438 | 666 |
| GM (% CV) | (27.4) | (22.1) | (27.1) | (32.3) | (14.6) | (23.5) | (25.2) | (15.6) | (20.2) |

The key plasma Compound A PK results for healthy adult subjects (Part B) administered a single 100 mg oral dose of study drug under fasted and fed conditions are summarized in Table 4. The plasma Compound A concentration profiles of Compound A 100 mg administered under fasted and fed conditions both showed rapid absorption, with peak plasma Compound A concentrations occurring at similar times (median tmax: fasted=2.99 hours; fed=3.49 hours). Thereafter, Compound A showed similar biphasic absorption profiles under fasted and fed conditions, as described above for the fasted cohorts. The higher plasma Compound A concentrations in the fed state compared to the fasted state were most evident during the period from tmax to 12 hours postdose.

TABLE 4

Summary of Plasma Compound A Pharmacokinetic Parameters in Part B (100 mg Cohort)

| Parameter | Compound A | |
|---|---|---|
| | 100 mg Fasted (N = 6) | 100 mg Fed (N = 6) |
| Cmax (ng/mL) GM (% CV) | 371 (16.0) | 536 (25.5) |
| tmax (h) Median (Min, Max) | 2.99 (1.50, 8.03) | 3.49 (1.95, 5.97) |
| tlag (h) Median (Min, Max) | 0 (0.00, 0.00) | 0.49 (0.00, 0.88) |
| AUC(0-24 h) (h × ng/mL) GM (% CV) | 6140 (13.9) | 7610 (23.8) |

TABLE 4-continued

Summary of Plasma Compound A Pharmacokinetic Parameters in Part B (100 mg Cohort)

| Parameter | Compound A | |
|---|---|---|
| | 100 mg Fasted (N = 6) | 100 mg Fed (N = 6) |
| AUC(0-30 h) (h × ng/mL) GM (% CV) | 7360 (15.3) | 8980 (23.0) |
| AUC(0-72 h) (h × ng/mL) GM (% CV) | 12200 (18.9) | 14500 (26.6) |
| AUC(0-t) (h × ng/mL) GM (% CV) | 14400 (23.5) | 17100 (31.6) |
| AUC(0-inf) (h × ng/mL) GM (% CV) | 14500 (23.6) | 17300 (31.0) |
| $t_{1/2}$ (h) Mean (SD) | 25.7 (4.90) | 26.0 (5.58) |
| CL/F (L/h) GM (% CV) | 6.89 (23.7) | 5.78 (31.0) |
| Vz/F(L) GM (% CV) | 252 (15.8) | 212 (26.4) |

Analysis of the log-transformed plasma Compound A PK parameters in healthy adult subjects administered Compound A 100 mg under fasted and fed conditions are summarized in Table 5. Administration of a single dose of Compound A 100 mg after consuming a standardized high-fat and high-calorie meal over 30 minutes prior to treatment resulted in a 44.4% increase in the geometric LS mean Cmax (90% CI: 1.210, 1.723) and a 19.2% increase in the geometric LS mean AUC(0-inf) (90% CI: 1.003, 1.418).

TABLE 5

Analysis of Log-transformed Plasma Compound A Pharmacokinetic Parameters in Healthy Adult Subjects Administered Compound A 100 mg Under Fasted and Fed Conditions in Part B (100 mg Cohort)

| Treatment Contrast (Test:Ref) | Parameter | Test (n) | Reference (n) | Geometric LS Means Test | Geometric LS Means Reference | Geometric LS Mean Ratio (90% CI) |
|---|---|---|---|---|---|---|
| Fed:Fasted | Cmax (ng/mL) | 6 | 6 | 535.97 | 371.16 | 1.444 (1.210, 1.723) |
| | AUC(0-t) (h × ng/mL) | 6 | 6 | 17,070.80 | 14,394.84 | 1.186 (0.992, 1.418) |
| | AUC(0-inf) (h × ng/mL) | 6 | 6 | 17,315.01 | 14,522.85 | 1.192 (1.003, 1.418) |

Log-transformed pharmacokinetic parameters were fit using a mixed effects model with treatment as a fixed effect and subject as a random effect. Geometric LS means and geometric LS mean ratio were back-transformed least squares mean and treatment mean difference.

Healthy Elderly Subjects:

The key plasma Compound A PK results for healthy elderly subjects (Part C) administered a single 100 mg oral dose of study drug are summarized in Table 6; results for healthy younger adult subjects (Parts A and B combined) administered the same dose are also shown for reference. After single doses of Compound A 100 mg, elderly subjects had a median tmax at 2.60 hours postdose, similar to 2.99 hours in healthy younger adults. In general, exposure and half-life were higher in elderly subjects as compared to the younger adults. Analysis of the log-transformed plasma Compound A PK parameters in healthy elderly subjects versus healthy younger adult subjects administered Compound A 100 mg are summarized in Table 7.

TABLE 6

Summary of Plasma Compound A Pharmacokinetic Parameters in Healthy Elderly Subjects (Part C) and Healthy Younger Adult Subjects (Parts A and B)

| Parameter | Compound A | |
|---|---|---|
| | Healthy Younger Adult Subjects 100 mg (N = 12) | Healthy Elderly Subjects 100 mg (N = 6) |
| Cmax (ng/mL) GM (% CV) | 373 (19.8) | 543 (27.6) |
| tmax (h) Median (Min, Max) | 2.99 (0.93, 8.03) | 2.60 (1.50, 4.02) |
| AUC(0-inf) (h × ng/mL) GM (% CV) | 15000 (20.0) | 21300 (26.6) |
| $t_{1/2}$ (h) Mean (SD) | 28.6 (6.73) | 38.1 (8.38) |
| CL/F (L/h) GM (% CV) | 6.66 (20.1) | 4.71 (26.5) |
| Vz/F (L) GM (% CV) | 268 (14.6) | 253 (23.9) |

TABLE 7

Analysis of Log-Transformed Pharmacokinetic Parameters in Healthy Elderly and Younger Adult Subjects Administered Single Oral Dose of Compound A 100 mg

| Treatment Contrast (Test:Ref) | Parameter | Test (n) | Reference (n) | Geometric LS Means Test | Geometric LS Means Reference | Geometric LS Mean Ratio (90% CI) |
|---|---|---|---|---|---|---|
| Elderly:Younger Adults | Cmax (ng/mL) | 6 | 12 | 543.03 | 373.32 | 1.455 (1.198, 1.766) |
| | AUC(0-inf) (h × ng/mL) | 6 | 12 | 21250.1 | 15017.18 | 1.415 (1.168, 1.715) |

Reference is healthy adult subjects in Parts A and B. Log-transformed pharmacokinetic parameters were fit using a general linear model with age category as a factor. Geometric LS means and geometric LS mean ratio were back-transformed least squares mean and age category mean difference.

Healthy Japanese Adult Subjects:

The key plasma Compound A PK parameters for healthy Japanese adult subjects (Part D) administered single oral doses (25, 100, or 400 mg) of study drug are summarized in Table 8; results for non-Japanese subjects (Parts A and B combined, but excluding those subjects who self-identified as Asian) administered the same doses are also shown for reference. The plasma Compound A exposure in healthy Japanese subjects administered Compound A 25, 100, and 400 mg were similar to those of healthy adult non-Japanese subjects. In healthy Japanese subjects, GM Cmax and AUC (0-inf) values increased subproportionally with increasing doses.

TABLE 8

Summary of Plasma Compound A Pharmacokinetic Parameters in Healthy Japanese (Part D) and Non-Japanese Subjects (Parts A and B, Excluding Those Subjects Who Self-identified as Asian)

| | Compound A Non-Japanese Subjects[a] | | |
|---|---|---|---|
| Parameter | 25 mg (N = 6) | 100 mg (N = 12) | 400 mg (N = 9) |
| Cmax (ng/mL) GM (% CV) | 152 (29.0) | 373 (19.8) | 827 (25.8) |
| tmax (h) Median (Min, Max) | 2.65 (2.02, 4.08) | 2.99 (0.93, 8.03) | 3.00 (0.98, 18.02) |
| AUC(0-inf) (h × ng/mL) GM (% CV) | 4340 (18.5) | 15,000 (20.0) | 35,800 (26.6) |
| t½(h) Mean (SD) | 26.8 (6.95) | 28.6 (6.73) | 34.5 (15.8) |
| CL/F (L/h) GM (% CV) | 5.76 (18.5) | 6.66 (20.1) | 11.2 (26.5) |
| Vz/F(L) GM (% CV) | 216 (22.1) | 268 (14.6) | 511 (26.9) |

| | Compound A Japanese Subjects | | |
|---|---|---|---|
| Parameter | 25 mg (N = 6) | 100 mg (N = 6) | 400 mg (N = 6) |
| Cmax (ng/mL) GM (% CV) | 212 (9.96) | 492 (8.53) | 1180 (32.9) |
| tmax (h) Median (Min, Max) | 2.08 (1.50, 3.05) | 2.52 (1.00, 5.00) | 2.25 (1.00, 4.07) |
| AUC(0-inf) (h × ng/mL) GM (% CV) | 4580 (23.8) | 14,200 (16.6) | 46,500 (32.9) |
| t½(h) Mean (SD) | 21.5 (5.40) | 23.9 (4.04) | 30.0 (7.21) |
| CL/F (L/h) GM (% CV) | 5.45 (23.8) | 7.05 (16.5) | 8.61 (32.9) |
| Vz/F(L) GM (% CV) | 165 (7.55) | 240 (18.9) | 364 (13.1) |

[a]Subjects who self-identified as Asian were excluded from the analysis.

Comparison of plasma Compound A PK results for healthy Japanese adult subjects (Part D) and non-Japanese subjects (Parts A and B combined, but excluding those subjects who self-identified as Asian) administered single oral doses (25, 100, or 400 mg) of study drug are summarized in Table 9. With weight as a covariate, healthy Japanese subjects administered single doses of Compound A 25, 100, and 400 mg had geometric LS mean Cmax values that were 35.6%, 30.0%, and 40.4% higher, respectively, than those in non-Japanese reference subjects administered the same doses. The effect did not appear to be dose-dependent. Similar results were observed in the analysis of Cmax performed without weight as a covariate.

Geometric LS mean AUC(0-inf) values were comparable between healthy Japanese subjects and non-Japanese reference subjects administered the same doses at 25 and 100 mg, both with and without weight as a covariate. However, based on the analysis with weight as a covariate, a 27.9% higher geometric LS mean AUC(0-inf) was observed in Japanese subjects administered Compound A 400 mg than in the non-Japanese reference subjects administered the same dose. Similar results were observed in the analysis of AUC(0-inf) in the 400 mg cohort performed without weight as a covariate.

Review of the scatter plots of Cmax and AUC(0-inf) in Japanese and non-Japanese reference subjects indicated that the distribution of Cmax and AUC(0-inf) in the majority of Japanese subjects was similar to that of the non-Japanese reference subjects. It is therefore considered that the higher Cmax (25, 100, and 400 mg cohorts) and AUC(0-inf) (400 mg cohort) values observed in Japanese subjects will not be clinically significant for most subjects.

TABLE 9

Analysis of Log-Transformed Pharmacokinetic Parameters in Healthy Japanese Subjects (Part D) and Non-Japanese Subjects (Parts A and B) Administered Single Oral Dose of Compound A 25, 100, or 400 mg

| Treatment Contrast (Test:Ref) | Parameter | Compound A Treatment (mg) | Test (n) | Reference (n) | Geometric LS Means Test | Geometric LS Means Reference | Geometric LS Mean Ratio (90% CI) |
|---|---|---|---|---|---|---|---|
| *Analysis with weight as covariate* | | | | | | | |
| Japanese:non-Japanese | Cmax (ng/mL) | 25 | 6 | 6 | 206.6 | 152.4 | 1.356 (1.082, 1.699) |
| | | 100 | 6 | 12 | 491.01 | 377.76 | 1.300 (1.074, 1.573) |
| | | 400 | 6 | 9 | 1169.59 | 833.33 | 1.404 (1.145, 1.721) |
| | AUC(0-inf) (h × ng/mL) | 25 | 6 | 6 | 4499.68 | 4348.37 | 1.035 (0.819, 1.308) |
| | | 100 | 6 | 12 | 14166.07 | 15151.67 | 0.935 (0.767, 1.140) |
| | | 400 | 6 | 9 | 46025.41 | 35980.16 | 1.279 (1.035, 1.580) |
| *Analysis without weight as covariate* | | | | | | | |
| Japanese:non-Japanese | Cmax (ng/mL) | 25 | 6 | 6 | 211.81 | 151.91 | 1.394 (1.122, 1.732) |
| | | 100 | 6 | 12 | 491.66 | 373.32 | 1.317 (1.091, 1.589) |
| | | 400 | 6 | 9 | 1184.74 | 826.58 | 1.433 (1.176, 1.747) |
| | AUC(0-inf) (h × ng/mL) | 25 | 6 | 6 | 4584.8 | 4337.82 | 1.057 (0.845, 1.323) |
| | | 100 | 6 | 12 | 14180.36 | 15017.18 | 0.944 (0.778, 1.147) |
| | | 400 | 6 | 9 | 46473.56 | 35760.66 | 1.300 (1.059, 1.595) |

Log-transformed pharmacokinetic parameters were fit using a general linear model with Japanese (Yes/No) as a factor together with baseline weight as a covariate. Geometric LS means and geometric LS mean ratio were back-transformed least squares mean and mean difference. Non-Japanese subjects in Parts A and B treated at the same dose as administered in Part D, are the Reference group and Japanese subjects are the Test group. Non-Japanese subjects in Parts A and B who self-identified as Asian were not included in the reference group.

CSF Compound A Pharmacokinetics

The CSF Compound A PK results for healthy adult subjects (Part B) administered single oral doses (50, 75, 100, 200, or 400 mg) of study drug are summarized in Table 10. Across the 50 to 400 mg doses, median CSF tmax values were 4.37 to 6.87 hours postdose (with the exception of the 50 mg dose for which median CSF tmax was 11.90 hours), occurring later than median plasma tmax values of 2 to 4 hours postdose (Table 3). Thereafter, CSF Compound A concentrations remained relatively stable for up to 18 hours postdose before declining.

Subjects underwent serial CSF sampling up to 30 hours postdose; therefore, it was not possible to characterize the terminal elimination phase of Compound A in CSF and the CSF Compound A half-life was not derived. Likewise, values for AUC(0-inf) could not be determined and values for AUC(0-t) were limited to 30 hours postdose. Both CSF Compound A Cmax and AUC(0-30 h) values increased with increasing doses in a subproportional manner. This was consistent with the subproportional increase observed in plasma Compound A Cmax and AUC(0-inf). Across various Compound A doses from 50 to 400 mg, the GM ratios of CSF Cmax to plasma Cmax were similar across doses, ranging from 2% to 2.77%. Similarly, the GM ratios of CSF AUC(0-t) to plasma AUC(0-t) were similar across doses, ranging from 2.41% to 2.80%.

TABLE 10

Summary of CSF Compound A Pharmacokinetic Parameters in Healthy Adult Subjects (Part B)

| Parameter | Compound A[a] | | | | |
|---|---|---|---|---|---|
| | 50 mg (N = 1) | 75 mg (N = 2) | 100 mg (N = 6) | 200 mg (N = 6) | 400 mg (N = 6) |
| Cmax (ng/mL) | | | | | |
| n | 1 | 2 | 6 | 6 | 6 |
| GM (% CV) | 6.27 (0.00) | 6.66 (4.78) | 7.20 (31.9) | 12.8 (51.8) | 15.3 (19.4) |
| tmax (hour) | | | | | |
| n | 1 | 2 | 6 | 6 | 6 |
| Median (Min, Max) | 11.90 (1.90, 11.90) | 5.37 (4.87, 5.87) | 6.87 (4.87, 17.90) | 4.37 (1.87, 17.90) | 5.37 (2.87, 17.90) |
| AUC(0-30 h) (h × ng/mL) | | | | | |
| n | 0 | 0 | 3 | 6 | 5 |
| GM (% CV) | | | 221 (12.0) | 257 (27.9) | 378 (23.0) |
| AUC(0-t) (h × ng/mL) | | | | | |
| n | 1 | 2 | 6 | 6 | 6 |
| GM (% CV) | 74.8 (.00) | 96.8 (41.1) | 81.7 (492) | 257 (27.9) | 334 (38.2) |
| CSF:plasma Cmax ratio (expressed as %) | | | | | |
| n | 1 | 2 | 6 | 6 | 6 |
| GM (% CV) | 2.00 (0.00) | 2.64 (46.5) | 1.94 (33.7) | 2.14 (45.2) | 2.03 (21.5) |
| CSF:plasma AUC ratio[b] (expressed as %) | | | | | |
| n | 0 | 1 | 4 | 6 | 5 |
| GM (% CV) | | 2.64 (0.00) | 2.66 (18.9) | 2.38 (15.5) | 2.79 (10.7) |

[a]Compound A was administered under fasted conditions for all treatment groups in this analysis.

[b]Ratios were determined from AUC(0-t) (or AUC(0-30 h), which was the last time point for CSF collection) rather than AUC(0-inf), since AUC(0-inf) could not be estimated for Compound A in CSF.

Urine Compound A Pharmacokinetics

The urine Compound A PK results for healthy adult subjects (Part A) administered single oral doses (10, 25, 50, 75, 100, 200, 400, 800, or 1200 mg) of study drug and healthy elderly subjects administered a single oral 100 mg dose of study drug are summarized in Table 11. Over the Compound A dose range of 10 to 1200 mg, less than 1% of unchanged Compound A was eliminated in the urine, suggesting that renal excretion is not an important elimination pathway for Compound A in humans. GM CLR values were similar in healthy elderly and younger adult subjects administered single oral doses of Compound A 100 mg.

TABLE 11

Urine Compound A Pharmacokinetic Parameters in Healthy Adult Subjects (Part A) and Elderly Subjects (Part C)

| Parameter | Compound A | | | | | | | | |
|---|---|---|---|---|---|---|---|---|---|
| | 10 mg (N = 6) | 25 mg (N = 6) | 50 mg (N = 6) | 100 mg (N = 6) | Elderly 100 mg (N = 6) | 200 mg (N = 6) | 400 mg (N = 6) | 800 mg (N = 6) | 1200 mg (N = 6) |
| Ae(0-96 h) (mg) | 0.0218 | 0.0476 | 0.104 | 0.295 | 0.228 | 0.177 | 0.615 | 0.762 | 1.18 |
| GM (% CV) | (34.0) | (27.0) | (36.2) | (78.4) | (32.7) | (79.3) | (55.9) | (22.6) | (47.9) |
| Fe(0-96 h) (%) | 0.218 | 0.190 | 0.208 | 0.295 | 0.228 | 0.0885 | 0.154 | 0.0953 | 0.0979 |
| GM (% CV) | (34.0) | (27.1) | (36.1) | (78.4) | (32.7) | (79.3) | (56.0) | (22.8) | (47.9) |
| CLR (L/h) | 0.0137 | 0.0121 | 0.0161 | 0.0222 | 0.0132 | 0.0102 | 0.0202 | 0.0127 | 0.0172 |
| GM (% CV) | (38.8) | (33.3) | (42.0) | (81.4) | (35.4) | (97.5) | (71.5) | (35.5) | (56.0) |

Pharmacodynamics

The key CSF cGMP results for healthy adult subjects (Part B) administered single oral doses of placebo or Compound A (50, 75, 100, 200, or 400 mg) are summarized in Table 12.

Across Compound A doses from 50 to 400 mg, mean maximum % CSF cGMP (Amax) increases from baseline ranged from 293% to 461%, and were higher than in placebo-treated subjects (76%). However there was no dose-dependent trend of increasing Amax values with increasing Compound A doses and there was no apparent correlation between Amax with Cmax, based on visual inspection of the scatter plot for these results. Amax appears to approach saturation within the Compound A dose range of 50 to 400 mg.

The median time to achieve Amax (tAmax) ranged from 5.37 to 12.9 hours across the Compound A doses tested with no dose-related trend. The mean ΔAUAC(0-30 h), which represented the average CSF cGMP increase from baseline over 30 hours postdose, was higher in all Compound A-treatment groups than in the placebo group. The ΔAUAC(0-30 h) for subjects administered Compound A 400 mg was higher than that of subjects administered lower doses. This observation is consistent with the visual impression of the concentration-time profiles of CSF cGMP, in which the PD effects of Compound A 400 mg was sustained for up to 24 hours postdose before starting to decline, whereas at the lower doses of 50 to 200 mg, CSF cGMP appeared to decline some time from 8 to 24 hours postdose.

TABLE 12

Summary of CSF cGMP Pharmacodynamic Parameters (Part B)

| Parameter | Compound A[a] | | | | | |
|---|---|---|---|---|---|---|
| | Placebo (N = 5) | 50 mg (N = 3) | 75 mg (N = 3) | 100 mg (N = 6) | 200 mg (N = 6) | 400 mg (N = 6) |
| Amax (%) | | | | | | |
| n | 5 | 3 | 3 | 6 | 6 | 6 |
| Mean (SD) | 76.3 (18.8) | 367 (92.6) | 461 (86.3) | 293 (67.8) | 424 (127) | 420 (123) |
| TAmax (hour) | | | | | | |
| n | 5 | 3 | 3 | 6 | 6 | 6 |
| Median (min, max) | 7.87 (4.87, 17.9) | 7.87 (4.87, 7,87) | 5.87 (3.87, 13.9) | 5.87 (2.87, 9.87) | 5.37 (2.87, 17.9) | 12.9 (3.87, 23.9) |
| ΔAUAC(0-30 h) (%) | | | | | | |
| n | 4 | 3 | 3 | 5 | 6 | 5 |
| Mean (SD) | -9.83 (13.7) | 117 (51.7) | 166 (9.61) | 87.0 (33.9) | 176 (89.5) | 214 (82.3) |

[a]Compound A was administered under tested conditions for all treatment groups in this analysis.

Parts A and C:

In Part A (healthy adult subjects), single oral doses of Compound A from 10 to 1200 mg were well tolerated. In Part C (healthy elderly subjects), a single dose of Compound A 100 mg was also well tolerated. In Parts A and C, there were no deaths or SAEs and no subjects withdrew from the study due to a TEAE. Across all doses of Compound A in Parts A and C, 23 (42.6%) subjects experienced at least 1 TEAE, compared to 3 (16.7%) subjects treated with placebo. In Part C (healthy elderly subjects treated with 100 mg of Compound A), 1 (16.7%) subject experienced at least 1 TEAE, and this was similar to the incidence in subjects in Part A and C treated with placebo. The most common TEAEs (reported in more than 1 subject) in Part A and C which occurred in subjects treated with Compound A were headache (11.6%), postural orthostatic tachycardia (5.6%), dizziness (5.6%), insomnia (5.6%), increase in orthostatic heart rate response (3.7%), and paresthesia (3.7%). Headache appeared to have a higher incidence than subjects on placebo. In subjects treated with Compound A, there were 3 (5.6%) subjects who had TEAE of postural orthostatic tachycardia syndrome with a similar incidence in subjects on placebo (1 [5.6%] subject affected). These subjects had increase in heart rate by greater than 30 beats per minute from the supine to standing position, with heart rate greater than 100 beats per minute on standing. This TEAE occurred in the healthy adult subjects at Compound A 25 and 50 mg, but not at other doses, and there were no dose-related trends. In subjects treated with Compound A 50 mg, there were 2 (3.7%) subjects who had TEAE of increased orthostatic heart rate response. Increased orthostatic heart rate response did not occur in subjects at doses above Compound A 50 mg or in healthy elderly subjects administered Compound A 100 mg. There were no changes of clinical importance in mean clinical laboratory values, vital signs, or ECG results over time.

Parts B

In Part B, single oral doses of Compound A from 50 to 400 mg were well tolerated in healthy adult subjects who underwent serial CSF sampling via an indwelling lumbar catheter during their first treatment period in the fasted state, and in the 100 mg cohort (without serial CSF sampling) during the second treatment period in the fed state. There were no deaths and no subjects withdrew from the study due to a TEAE. One placebo-treated subject experienced an SAE of post-dural puncture headache that was assessed by the investigator as not related to study drug. Across both treatment periods and all Compound A doses, 20 (83.3%) subjects experienced at least 1 TEAE, which was similar to the incidence in placebo-treated subjects (4 [80%] subjects). In the 100 mg Cohort, the incidence of any TEAEs in the fasted state (4 [66.7%] subjects) and in the fed state (3 [50%] subjects) was comparable. The most common TEAEs (reported in more than 1 subject) that were reported in Compound A-treated subjects were post lumbar puncture syndrome (37.5%), headache (29.2%), vomiting (20.8%), musculoskeletal stiffness (20.8%), back pain (20.8%), dizziness (16.7%), nausea (12.5%), pain in extremity (8.3%), procedural vomiting (8.3%), and procedural nausea (8.3%). These TEAEs were likely to be related to the serial CSF sampling procedure and had a similar incidence in Compound A-treated and placebo-treated subjects. The incidence of other TEAEs in Compound A-treated subjects was similar to, or lower than the incidence in placebo-treated subjects. There were no dose-related trends in various TEAEs to indicate increasing incidence with increasing Compound A doses. In subjects treated with Compound A 100 mg the incidence of TEAEs that were not assessed by the investigator to be related to the CSF sampling procedure was low and similar during the fasted and fed treatment conditions. There were no changes of clinical importance in mean clinical laboratory values, vital signs, or ECG results over time.

Parts D

In Part D (healthy Japanese adult subjects), single oral doses of Compound A from 25 to 400 mg were well tolerated. Across all doses of Compound A, 7 (38.9%) subjects experienced at least 1 TEAE, whereas no placebo-treated subjects reported TEAEs. The most common TEAE (reported in more than 1 subject) that occurred in Compound A-treated subjects was headache (3 [16.7%] subjects). The incidence of various TEAEs in Compound A-treated subjects was low (generally reported only in 1 subject) and generally similar to placebo-treated subjects. There were no dose-related trends in various TEAEs to indicate increasing incidence with increasing Compound A doses. The incidence of various TEAEs in Japanese subjects (Part D) and non-Japanese subjects (Part A) treated at the same dose of Compound A was similar. There were no changes of clinical importance in mean clinical laboratory values, vital signs, or ECG results over time.

CONCLUSIONS

Pharmacokinetics

Healthy Adult Subjects

1) After oral administration of single doses of 10 to 1200 mg, Compound A was rapidly absorbed with most subjects having quantifiable plasma concentrations within 0.5 hours postdose, with median tmax occurring at 2 to 4 hours postdose. Thereafter, Compound A showed biphasic disposition in its PK profile. During the initial disposition phase, plasma Compound A concentrations declined until approximately 12 hours postdose and then remained relatively stable until 24 hours postdose. From 24 hours postdose, Compound A showed first order kinetics during the terminal elimination phase with mean half life values ranging from 26.8 to 33.6 hours, which was comparable among doses.

2) Overall the GM Cmax and AUC(0-inf) values increased subproportionally with increasing Compound A doses from 10 to 1200 mg. In the dose range of 50 to 400 mg, which represents the potential target dose range for clinical development, dose normalized Cmax and AUC(0-inf) values decreased with increasing doses.

3) When Compound A 100 mg was administered in the fed state after a high fat and high calorie meal, there was a 44.4% increase in the geometric LS mean Cmax and a 19.2% increase in the geometric LS mean AUC(0-inf), while median tmax and mean half-life were similar in the fed and fasted states. The small increase in Cmax and AUC(0-inf) was not considered to be clinically significant and Compound A may be administered with or without food.

4) After single doses of Compound A at 100 to 400 mg, distribution of Compound A into CSF was slightly delayed with median CSF tmax ranging from 4.37 to 6.87 hours postdose, which occurred later than median plasma tmax. Thereafter, CSF concentrations remained relatively stable up to 18 hours postdose before declining. Across various doses from 50 to 400 mg, the mean CSF: plasma ratios (expressed as percentages) of Compound A Cmax or AUC (0-t) were similar, ranging from 2% to 3%. Based on in vitro protein binding, free Compound A (non-protein bound) concentrations in plasma would be 2.7% to 3.4% of total plasma Compound A concentrations. Thus, the CSF Compound A concentrations were similar to the free Compound A concentrations in plasma.

5) Less than 1% of the dose of Compound A was excreted unchanged in urine, suggesting that renal excretion is not an important elimination pathway for Compound A in humans.

Healthy Elderly Subjects

1) In healthy elderly subjects administered Compound A 100 mg, the geometric LS mean Cmax was approximately 45.5% higher and geometric LS mean AUC(0-inf) was approximately 41.5% higher than in younger healthy adult subjects. The mean terminal half-life in healthy elderly subjects was approximately 10 hours longer than in younger healthy adult subjects.

Healthy Japanese Adult Subjects

1) In healthy Japanese subjects the geometric LS mean Cmax was 35.2% higher than non-Japanese subjects across the 3 Compound A doses and this effect did not appear to be dose-dependent. In healthy Japanese subjects the geometric LS mean AUC(0-inf) was comparable to non-Japanese subjects at 25 and 100 mg doses, but higher than non-Japanese subjects by 27.9% at 400 mg. The mean half-life appeared to be similar between Japanese and non-Japanese subjects at all dose levels, but GM CL/F appeared to be higher in Japanese than non-Japanese subjects administered Compound A 400 mg.

2) In healthy Japanese subjects, GM Cmax and AUC(0-inf) values increased subproportionally with increasing Compound A doses just as in the non-Japanese subjects.

3) It is considered that there are no clinically significant differences in Cmax or AUC(0-inf) between Japanese subjects and non-Japanese subjects. No Compound A dose adjustments are required when Compound A is administered to Japanese subjects.

Pharmacodynamics

1) Single doses of Compound A 50 to 400 mg resulted in elevation of CSF cGMP from baseline during the first 4 hours postdose. CSF cGMP concentrations then remained relatively stable for at least 4 hours further, before starting to decline, but still remained above baseline at 30 hours postdose.

2) Across Compound A doses from 50 to 400 mg, mean maximum % CSF cGMP (Amax) increases from baseline ranged from 293% to 461% and were higher than in placebo-treated subjects (76%). However, there was no dose-dependent trend of increasing Amax with increasing Compound A doses and the Amax appeared to approach saturation within the dose range investigated (Compound A 50 to 400 mg). The CSF cGMP PD effects appeared to be sustained for a longer period in subjects administered Compound A 400 mg compared to the lower doses. There were no correlations between plasma Compound A PK parameters (such as Cmax and AUC(0-inf)) and CSF cGMP PD parameters (such as Amax and ΔAUAC(0-30 h)).

Safety

1) Compound A was well tolerated in healthy adult subjects administered single oral doses of Compound A across the dose range of 10 to 1200 mg, and the maximum tolerated dose was not reached within the 120-fold range of increasing Compound A doses.

2) There were no Compound A dose-related trends in the incidence of various TEAEs. Most TEAEs were of mild severity.

3) There were no clinically significant changes in hematology, biochemistry and urinalysis values associated with Compound A at 10 to 1200 mg.

4) There were no clinically significant changes in blood pressure, heart rate, respiratory rate and body temperature associated with Compound A at 10 to 1200 mg.

5) There were no effects of Compound A on ECG morphology, heart rate, PR interval and QRS interval. The exposure-response relationship of the ΔΔQTcF showed that even at the Cmax at the highest doses of 800 to 1200 mg the upper 90% CI of the ΔΔQTcF was less than 10 ms in healthy subjects.

6) A single oral dose of Compound A 100 mg was well tolerated in healthy elderly subjects. The safety profile of Compound A in healthy elderly subjects was similar to that of healthy younger adult subjects.

7) Single oral doses of Compound A 25, 100, and 400 mg were well tolerated in healthy Japanese adult subjects. The safety profile of Compound A in healthy Japanese adult subjects was similar to that of non-Japanese subjects, including the exposure-QTcF relationship.

A study to assess the pharmacokinetics and pharmacodynamics of Compound A in healthy subjects Arm Experimental: Compound A Four sequential cohorts of healthy participants (≥50 years and ≤85 years old) were treated with multiple ascending doses of Compound A up to the maximum tolerated dose (MTD). A total of 6 participants per cohort were randomized to Compound A. Proposed doses of Compound A were:

Part A
Cohort 1: 50 mg (1×50 mg capsule)
Cohort 2: 100 mg (2×50 mg capsules)
Cohort 3: 200 mg (4×50 mg capsules)
Cohort 4: 400 mg (8×50 mg capsules)
Cohort 6: 25 mg (5×5 mg capsules)
Part B
Cohort 5: 400 mg (8×50 mg capsule)
Part C
Cohort 7: 50 mg (1×50 mg capsules)
Part D
Cohort 8: 5 mg (1×5 mg capsules)
Cohort 9: 10 mg (2×5 mg capsules)
Placebo Comparator. Placebo Four sequential cohorts of healthy participants (≥50 years and ≤85 years old) were treated with multiple ascending doses of Compound A matched placebo up to the MTD. A total of 2 participants per cohort were randomized to Compound A matched placebo.

Intervention/Treatment

Drug: Compound A

Participants received Compound A capsules, orally once daily (QD) on Days 1 to 14 after an overnight fast of at least 10 hours. Compound A was administered orally with 240 milliliter (mL) (8 fluid ounces) of water.

Drug: Compound A matched placebo

Participants received Compound A matched placebo capsules, orally once daily (QD) on Days 1 to 14 after an overnight fast of at least 10 hours. Compound A matched placebo was administered orally with 240 mL (8 fluid ounces) of water.

Outcome Measures

1) Maximum drug concentration (Cmax) [Time Frame: Day 1 and Day 14]

Blood samples were collected on Day 1 at predose and postdose 0.5 (30 minutes), 1, 1.5, 2, 3, 4, 5, 6, 8, 12, and 18 hours; Day 14 (at predose and postdose 0.5, 1, 1.5, 2, 3, 4, 5, 6, 8, 12, and 18 hours); and Day 15 (24 hours postdose from Day 14).

2) Mean time to reach maximum (peak) drug concentration (tmax) [Time Frame: Day 1 and Day 14]

Blood samples were collected on Day 1 at predose and postdose 0.5 (30 minutes), 1, 1.5, 2, 3, 4, 5, 6, 8, 12, 18 and 24 hours; Day 14 (at predose and postdose 0.5, 1, 1.5, 2, 3, 4, 5, 6, 8, 12, and 18 hours); and Day 15 (24 hours postdose from Day 14).

3) Mean area under the concentration-time curve from zero time to 24 hours postdose (AUC(0-24 h)) [Time Frame: Day 1 and Day 14]

Blood samples were collected on Day 1 at predose and postdose 0.5 (30 minutes), 1, 1.5, 2, 3, 4, 5, 6, 8, 12, 18 and 24 hours; Day 14 (at predose and postdose 0.5, 1, 1.5, 2, 3, 4, 5, 6, 8, 12, and 18 hours); and Day 15 (24 hours postdose from Day 14).

4) Mean area under the concentration-time curve from zero time extrapolated to infinity (AUC(0-inf)) [Time Frame: Day 14]

Blood samples were collected on Day 14 (at predose and postdose 0.5, 1, 1.5, 2, 3, 4, 5, 6, 8, 12, and 18 hours) and Day 15 (24 hours postdose from Day 14).

5) Mean ratio of cerebrospinal fluid (CSF): plasma concentrations [Time Frame: Day −2 (time-matched to the Day 13 lumbar puncture [LP]) and Day 13 (predose)]

6) Percentage change from Baseline in pharmacodynamic measure [Time Frame: Day −2 (baseline with no drug) to Day 13 (on drug)]

The results are summarized in the following Tables 13 to 18.

TABLE 13

Summary of Plasma Pharmacokinetic Parameters of Compound A on Day 1 Parts A, B and D

| Parameter | Compound A | | | | | | | |
|---|---|---|---|---|---|---|---|---|
| | 5 mg (N = 5) | 10 mg (N = 5) | 25 mg (N = 6) | 50 mg (N = 6) | 100 mg (N = 6) | 200 mg (N = 6) | 400 mg Non-Japanese (N = 6) | 400 mg Japanese (N = 6) |
| Cmax (ng/mL) | | | | | | | | |
| Mean (SD) | 27.4 (8.14) | 66.2 (11.5) | 129 (30.9) | 237 (115) | 373 (87.1) | 740 (257) | 1100 (142) | 1520 (236) |
| Median | 26.6 | 65.8 | 136 | 226 | 344 | 813 | 1140 | 1510 |
| Min, Max | 14.8, 34.7 | 53.0, 83.8 | 76.1, 160 | 117, 414 | 296, 533 | 283, 955 | 866, 1290 | 1270, 1840 |
| GM (% CV) | 26.3 (35.8) | 65.5 (17.1) | 125 (28.0) | 214 (54.1) | 366 (21.7) | 687 (49.0) | 1100 (13.6) | 1510 (15.6) |
| tmax (h) | | | | | | | | |
| Median | 4.00 | 2.00 | 3.01 | 3.53 | 2.53 | 2.01 | 1.76 | 2.00 |
| Min, Max | 2.00, 4.00 | 1.50, 4.00 | 2.00, 5.00 | 2.00, 4.02 | 1.50, 6.00 | 1.03, 23.65 | 1.03, 3.00 | 1.00, 5.00 |
| AUC(0-24 h) (h × ng/mL) | | | | | | | | |
| Mean (SD) | 352 (84.7) | 784 (77.8) | 1670 (244) | 3110 (993) | 5250 (511) | 9050 (2600) | 14600 (1820) | 18400 (1790) |
| Median | 340 | 735 | 1700 | 3060 | 5180 | 10400 | 14700 | 18900 |
| Min, Max | 246, 451 | 721, 895 | 1320, 1940 | 1880, 4340 | 4730, 6210 | 4560, 11000 | 12700, 17700 | 15800, 20700 |
| GM (% CV) | 344 (25.2) | 781 (9.72) | 1650 (15.1) | 2970 (34.3) | 5230 (9.33) | 8650 (36.2) | 14500 (12.2) | 18300 (9.93) |

TABLE 14

Summary of Plasma Pharmacokinetic Parameters of Compound A on Day 14 Parts A, B and D

| | Compound A | | | | | | | |
|---|---|---|---|---|---|---|---|---|
| Parameter | 5 mg (N = 5) | 10 mg (N = 5) | 25 mg (N = 6) | 50 mg (N = 6) | 100 mg (N = 6) | 200 mg (N = 6) | 400 mg Non-Japanese (N = 6) | 400 mg Japanese (N = 6) |
| Cmax (ng/mL) | | | | | | | | |
| Mean (SD) | 61.7 (22.6) | 137 (27.4) | 336 (59.6) | 788 (133) | 1020 (177) | 1730 (437) | 2820 (689) | 3100 (400) |
| Median | 49.4 | 144 | 318 | 807 | 1030 | 1950 | 3050 | 3250 |
| Min, Max | 41.7, 93.6 | 98.4, 165 | 266, 414 | 581, 935 | 715, 1190 | 1090, 2080 | 1900, 3610 | 2580, 3560 |
| GM (% CV) | 58.6 (36.3) | 135 (21.5) | 332 (17.6) | 778 (18.2) | 1010 (19.0) | 1680 (28.7) | 2740 (26.7) | 3080 (13.3) |
| tmax (h) | | | | | | | | |
| Median | 4.00 | 1.50 | 3.00 | 1.50 | 2.56 | 2.00 | 1.79 | 1.50 |
| Min, Max | 1.00, 5.00 | 1.00, 3.03 | 2.03, 4.02 | 1.47, 2.07 | 1.07, 5.00 | 1.00, 5.03 | 1.52, 4.00 | 1.50, 2.02 |
| AUC(0-24 h) (h × ng/mL) | | | | | | | | |
| Mean (SD) | 864 (214) | 1940 (401) | 5210 (948) | 11800 (2780) | 16000 (2980) | 23100 (4720) | 40300 (9870) | 42900 (4640) |
| Median | 773 | 1980 | 4760 | 10900 | 16800 | 21300 | 43900 | 43200 |
| Min, Max | 668, 1150 | 1410, 2500 | 4300, 6490 | 8410, 15800 | 12700, 21400 | 18000, 29300 | 26400, 50000 | 36800, 48500 |
| GM (% CV) | 844 (24.5) | 1900 (21.3) | 5140 (17.7) | 11500 (23.9) | 16600 (18.0) | 22800 (20.4) | 39200 (27.2) | 42700 (11.0) |
| AUC(0-inf) (h × ng/mL) | | | | | | | | |
| Mean (SD) | 2480 (766) | 5260 (1490) | 16200 (6060) | 40700 (14200) | 58600 (16000) | 72200 (18900) | 135000 (66200) | 125000 (26600) |
| Median | 2510 | 5360 | 14000 | 38100 | 62700 | 61900 | 141000 | 120000 |
| Min, Max | 1610, 3530 | 3700, 7410 | 11100, 26700 | 22500, 59000 | 30600, 74000 | 57300, 103000 | 59300, 239000 | 99000, 165000 |
| GM (% CV) | 2380 (32.3) | 5100 (28.6) | 15400 (35.5) | 38600 (38.7) | 56400 (33.7) | 70500 (24.5) | 121000 (56.8) | 122000 (21.1) |

TABLE 15

Summary of Plasma Pharmacokinetic Parameters of Compound A Part C

| Parameter | Compound A 50 mg (N = 10) |
|---|---|
| Cmax (ng/mL) | |
| Mean (SD) | 608 (142) |
| Median | 590 |
| Min, Max | 388, 920 |
| GM (% CV) | 594 (22.9) |
| tmax (h) | |
| Median | 1.98 |
| Min, Max | 1.02, 4.02 |
| AUC(0-24 h) (h × ng/mL) | |
| Mean (SD) | 10800 (2390) |
| Median | 10600 |
| Min, Max | 6920, 15400 |
| GM (% CV) | 10500 (22.7) |

TABLE 16

CSF cGMP (ug/L) - Mean, Mean Change, Mean % Change from Baseline by Timepoint Parts A and D

| | | Compound A | | | | | | |
|---|---|---|---|---|---|---|---|---|
| Visit | Placebo (N = 10) | 5 mg (N = 5) | 10 mg (N = 5) | 25 mg (N = 6) | 50 mg (N = 6) | 100 mg (N = 6) | 200 mg (N = 6) | 400 mg Non-Japanese (N = 6) |
| Day 13 | | | | | | | | |
| Mean | 1.490 | 1.964 | 2.704 | 3.283 | 5.778 | 6.066 | 5.702 | 4.945 |
| Std | 0.3265 | 0.6381 | 0.6871 | 0.8799 | 2.3494 | 2.0510 | 1.4554 | 1.5090 |
| Median | 1.430 | 1.730 | 2.620 | 3.225 | 4.870 | 5.420 | 5.640 | 4.370 |
| Min, Max | 1.06, 1.90 | 1.24, 2.82 | 2.04, 3.85 | 1.91, 4.46 | 4.25, 9.95 | 3.56, 9.00 | 3.89, 7.41 | 3.44, 7.58 |
| CV | 21.91 | 32.49 | 25.41 | 26.80 | 40.66 | 33.81 | 25.53 | 30.52 |
| Change from Baseline | | | | | | | | |
| Mean | −0.041 | 0.491 | 1.276 | 2.058 | 3.750 | 4.352 | 3.810 | 3.302 |
| Std | 0.2373 | 0.2207 | 0.2516 | 0.7641 | 1.5919 | 1.5263 | 1.2518 | 1.3389 |
| Median | 0.030 | 0.350 | 1.390 | 1.979 | 3.260 | 3.960 | 3.755 | 2.920 |
| Min, Max | −0.41, 0.22 | 0.32, 0.80 | 0.87, 1.49 | 0.79, 2.91 | 2.62, 6.51 | 2.28, 6.11 | 2.45, 5.49 | 2.02, 5.67 |
| CV | −578.72 | 44.98 | 19.71 | 37.13 | 42.45 | 35.07 | 32.85 | 40.55 |
| % Change from Baseline | | | | | | | | |
| Mean | 0.154 | 33.162 | 94.222 | 170.369 | 191.445 | 260.350 | 201.165 | 198.283 |
| Std | 14.6640 | 10.0747 | 23.9898 | 63.5721 | 51.7750 | 77.6555 | 58.8963 | 61.6483 |
| Median | 2.055 | 29.954 | 104.348 | 183.494 | 189.244 | 258.784 | 192.932 | 191.646 |
| Min, Max | −22.36, 16.67 | 25.36, 49.69 | 63.14, 116.26 | 70.54, 246.90 | 117.49, 262.77 | 178.13, 382.19 | 131.38, 306.70 | 133.71, 296.86 |
| CV | 9496.49 | 30.38 | 25.46 | 37.31 | 27.04 | 29.83 | 29.28 | 31.09 |

TABLE 17

CSF cGMP (ug/L) - Mean, Mean Change, Mean % Change from Baseline by Timepoint Part C

| Visit | Compound A 50 mg (N = 10) |
|---|---|
| Day 13 | |
| Mean | 4.620 |
| Std | 1.0762 |
| Median | 4.265 |
| Min, Max | 3.11, 6.27 |
| CV | 23.29 |

TABLE 17-continued

CSF cGMP (ug/L) - Mean, Mean Change, Mean % Change from Baseline by Timepoint Part C

| Visit | Compound A 50 mg (N = 10) |
|---|---|
| Change from Baseline | |
| Mean | 3.206 |
| Std | 0.9055 |
| Median | 3.065 |
| Min, Max | 1.91, 4.51 |
| CV | 28.25 |

TABLE 17-continued

CSF cGMP (ug/L) - Mean, Mean Change, Mean % Change from Baseline by Timepoint Part C

| Visit | Compound A 50 mg (N = 10) |
|---|---|
| % Change from Baseline | |
| Mean | 229.107 |
| Std | 60.5077 |
| Median | 218.491 |
| Min, Max | 152.47, 350.81 |
| CV | 26.41 |

TABLE 18

CSF cGMP (ug/L) - Mean, Mean Change, Mean % Change from Baseline by Timepoint Part C

| Visit | Compound A 50 mg (N = 10) |
|---|---|
| Day 41 | |
| Mean | 4.511 |
| Std | 1.3698 |
| Median | 4.650 |
| Min, Max | 2.72, 6.56 |
| CV | 30.37 |
| Change from Baseline | |
| Mean | 3.097 |
| Std | 1.2607 |
| Median | 2.975 |
| Min, Max | 1.52, 5.32 |
| CV | 40.71 |
| % Change from Baseline | |
| Mean | 222.283 |
| Std | 96.7637 |
| Median | 182.044 |
| Min, Max | 126.67, 429.03 |
| CV | 43.53 |

The invention claimed is:

1. An oral dosage form comprising a therapeutically effective amount of Compound A or a pharmaceutically acceptable salt thereof and at least one pharmaceutically acceptable excipient, wherein said at least one pharmaceutically acceptable excipient is crospovidone, said therapeutically effective amount is a single daily dose ranging from about 25 mg to about 400 mg to achieve a mean Cmax of from about 1.8 ng/mL to about 7.6 ng/mL for each 1 mg of Compound A after administration to human subjects, and said Compound A is (S)-7-(2-methoxy-3,5-dimethylpyridin-4-yl)-1-(tetrahydrofuran-3-yl)-1H-pyrazolo[4,3-c]quinolin-4(5H)-one represented by Formula (1)

[Chem. 1]

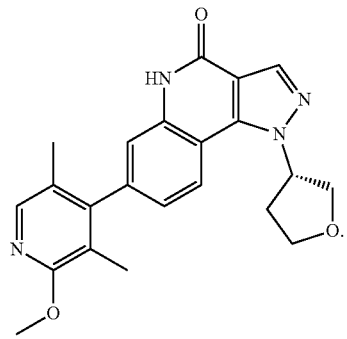

Formula (1)

2. The oral dosage form of claim 1, wherein said therapeutically effective amount is a single daily dose to achieve a mean AUC(0-inf) of from about 72.6 to about 217.0 ng*hr/mL for each 1 mg of Compound A after administration to human subjects.

3. The oral dosage form of claim 1, wherein said therapeutically effective amount is a single daily dose to achieve a mean AUC(0-t) of from about 71.0 to about 210.0 ng*hr/mL for each 1 mg of Compound A after administration to human subjects.

4. An oral dosage form comprising about 25 mg to about 400 mg of Compound A or a pharmaceutically acceptable salt thereof and at least one pharmaceutically acceptable excipient, wherein said at least one pharmaceutically acceptable excipient is crospovidone, and said Compound A is (S)-7-(2-methoxy-3,5-dimethylpyridin-4-yl)-1-(tetrahydrofuran -3-yl)-1H-pyrazolo[4,3-c]quinolin-4(5H)-one represented by Formula (1)

[Chem. 2]

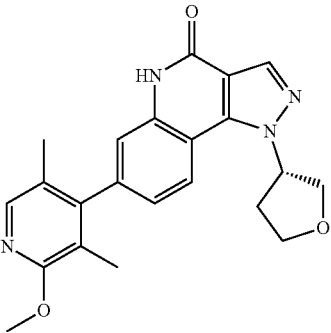

Formula (1)

wherein said Compound A or a pharmaceutically acceptable salt thereof at a single daily dose achieves a mean Cmax of from about 1.8 ng/mL to about 7.6 ng/mL for each 1 mg of Compound A after administration to human subjects.

5. An oral dosage form comprising about 25 mg to about 400 mg of Compound A or a pharmaceutically acceptable salt thereof and at least one pharmaceutically acceptable excipient, wherein said at least one pharmaceutically acceptable excipient is crospovidone, and said Compound A is (S)-7-(2-methoxy-3,5-dimethylpyridin-4-yl)-1-(tetrahydrofuran -3-yl)-1H-pyrazolo[4,3-c]quinolin-4(5H)-one represented by Formula (1)

Formula (1)

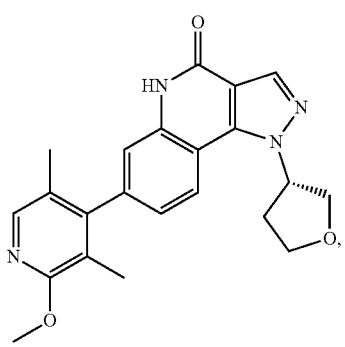

wherein said Compound A or a pharmaceutically acceptable salt thereof at a single daily dose achieves a mean AUC(0-inf) of from about 72.6 to about 217.0 ng*hr/mL for each 1 mg of Compound A after administration to human subjects.

6. An oral dosage form comprising about 25 mg to about 400 mg of Compound A or a pharmaceutically acceptable salt thereof and at least one pharmaceutically acceptable excipient, wherein said at least one pharmaceutically acceptable excipient is crospovidone, and said Compound A is (S)-7-(2-methoxy-3,5-dimethylpyridinin-4-yl)-1-(tetrahydrofuran -3-yl)-1H-pyrazolo[4,3-c]quinolin-4(5H)-one represented by Formula (1)

Formula (1)

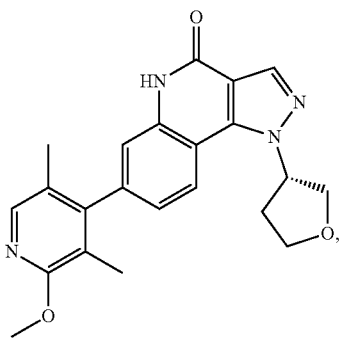

wherein said Compound A or a pharmaceutically acceptable salt thereof at a single daily dose achieves a mean AUC(0-t) of from about 71.0 to about 210.0 ng*hr/mL for each 1 mg of Compound A after administration to human subjects.

* * * * *

UNITED STATES PATENT AND TRADEMARK OFFICE
CERTIFICATE OF CORRECTION

PATENT NO. : 11,484,502 B2
APPLICATION NO. : 16/609514
DATED : November 1, 2022
INVENTOR(S) : Edgar Schuck et al.

It is certified that error appears in the above-identified patent and that said Letters Patent is hereby corrected as shown below:

On the Title Page

Column 2, item (56), OTHER PUBLICATIONS
Line 1, delete "etal" and insert -- et al --.

Column 2, item (57), ABSTRACT
Line 4, delete "quin olin" and insert -- quinolin --.

In the Claims

Column 46
Claim 4, Lines 34-35, delete "(tetrahydrofuran -3-yl)" and insert -- (tetrahydrofuran-3-yl) --.
Claim 5, Lines 65-66, delete "(tetrahydrofuran -3-yl)" and insert -- (tetrahydrofuran-3-yl) --.
Claim 5, Line 66, delete "-clquinolin" and insert -- -c]quinolin --.

Column 48
Claim 6, Lines 1-2, delete "dimethylpyridinin-4-yl)-1-(tetrahydrofuran -3-yl)" and insert
-- dimethylpyridin-4-yl)-1-(tetrahydrofuran-3-yl) --.

Signed and Sealed this
Tenth Day of January, 2023

Katherine Kelly Vidal
*Director of the United States Patent and Trademark Office*